United States Patent
Neuwelt et al.

(10) Patent No.: US 7,022,315 B2
(45) Date of Patent: Apr. 4, 2006

(54) ADMINISTRATION OF A THIOL-BASED CHEMOPROTECTANT COMPOUND

(75) Inventors: Edward A. Neuwelt, Portland, OR (US); Leslie Muldoon, Tigard, OR (US); Michael A. Pagel, Milwaukie, OR (US)

(73) Assignees: Oregon Health & Science University, Portland, OR (US); United States of America as represented by the Department of Veterans Affairs, Washington, DC (US)

( * ) Notice: Subject to any disclaimer, the term of this patent is extended or adjusted under 35 U.S.C. 154(b) by 232 days.

(21) Appl. No.: 10/257,879

(22) PCT Filed: Apr. 26, 2001

(86) PCT No.: PCT/US01/40624

§ 371 (c)(1),
(2), (4) Date: May 16, 2003

(87) PCT Pub. No.: WO01/80832

PCT Pub. Date: Nov. 1, 2001

(65) Prior Publication Data

US 2003/0176359 A1 Sep. 18, 2003

Related U.S. Application Data

(60) Provisional application No. 60/229,870, filed on Aug. 30, 2000, provisional application No. 60/199,936, filed on Apr. 26, 2000.

(51) Int. Cl.
*A61K 7/42* (2006.01)
*A61K 7/00* (2006.01)
*A61K 31/74* (2006.01)
*A61K 47/32* (2006.01)

(52) U.S. Cl. ............ 424/59; 424/401; 424/70.51; 424/78; 514/772.4; 514/8; 514/922; 514/558; 514/561

(58) Field of Classification Search ............ 424/59, 424/401, 70.51, 78; 514/772.4, 8, 922, 558, 514/561
See application file for complete search history.

(56) References Cited

U.S. PATENT DOCUMENTS 4,474,759 A * 10/1984 Petrovich .................... 424/711
4,961,926 A * 10/1990 Gabrilove ................... 424/85.1
5,510,101 A * 4/1996 Stroppolo et al. .......... 424/78.04
5,728,373 A * 3/1998 Alert et al. ................... 424/59
5,906,984 A 5/1999 Capizzi et al. .............. 514/114
5,994,409 A 11/1999 Stogniew et al. ........... 514/665
6,110,891 A * 8/2000 Pusztai et al. ................ 514/8
6,455,061 B1 * 9/2002 Richardson et al. ........ 424/422
6,573,253 B1 6/2003 Stogniew ..................... 514/114
6,759,061 B1 * 7/2004 Watson et al. .............. 424/725
2003/0157191 A1 8/2003 Kil et al. ..................... 424/649

FOREIGN PATENT DOCUMENTS

| EP | 0 624 377 A2 | 11/1994 |
|---|---|---|
| WO | WO 92/08448 | 5/1992 |
| WO | WO 94/00141 | 1/1994 |
| WO | WO 94/03179 | 2/1994 |
| WO | WO 96/14852 | 5/1996 |
| WO | WO 96/26643 | 9/1996 |
| WO | WO 98/11898 | 3/1998 |
| WO | WO 98/34622 | 8/1998 |
| WO | WO 99/29312 | 6/1999 |
| WO | WO 01/80832 | 11/2001 |
| WO | WO 04/039336 | 5/2004 |

OTHER PUBLICATIONS

Patchen et al., "Granulocyte colony -stimulating factor and amifostine(ethyol) . . . " (abstract only) Seminars in Oncology, 1994, vol. 21(5 suppl. 11), pp. 26-32.*

Mohr et al., "Combined treatment of stage IV melanoma patients with amifostine and . . . ", (abstract only), Melanoma Research, 1998, vol. 8(2), pp. 166-169.*

Antonadou et al., "Amifostine reduces radiochemotherapy-induced toxicities in patients with locally . . . ", (abstract only), Seminars in Oncology, 2003, vol. 30(6 suppl. 18), pp. 2-9.*

Alvarado, C.S. et al., "Chemotherapy for Patients with Recurrent or Refractory Neuroblastoma: A POG Phase II Study," *Journal of Pediatric Hematology/Oncology 19*(1): 62-67, Feb. 1997.

(Continued)

Primary Examiner—Vickie Kim
(74) Attorney, Agent, or Firm—Seed IP Law Group PLLC

(57) ABSTRACT

A method of administration of a thiol-based chemoprotectant agent including NAC (N-acetylcysteine) and STS (sodium thiosulfate) that markedly affects biodistribution and protects against injury from diagnostic or therapeutic intra-arterial procedures. A method for treating or mitigating the side effects of cytotoxic cancer therapy for tumors located in the head or neck and brain tumors. The thiol-based chemoprotectant agent is administered intra-arterially with rapid and first pass uptake in organs and tissues other than the liver.

2 Claims, 12 Drawing Sheets

OTHER PUBLICATIONS

Blakley, B.W. et al., "Strategies for Prevention of Toxicity Caused by Platinum-Based Chemotherapy: Review and Summary of the Annual Meeting of the Blood-Brain Barrier Disruption Program, Gleneden Beach, Oregon, Mar. 10, 2001," *The Laryngoscope 112*(11): 1997-2001, Nov. 2002.

Blay, J.Y. et al., "A Risk Model for Thrombocytopenia Requiring Platelet Transfusion After Cytotoxic Chemotherapy," *Blood 92*(2): 405-410, Jul. 15, 1998.

Budd, G.T. et al., "Clinical Effects of Amifostine (Ethyol®) in Patients Treated with Carboplatin," *European Journal of Cancer 32A*(Suppl. 4): S43-S45, Oct. 1996.

Butterworth, M. et al., "Cysteine *Isopropylester* Protects Against Paracetamol-Induced Toxicity," *Biochemical Pharmacology 43*(3): 483-488, 1992.

Case, B.C. et al., "The Pharmacokinetics and Pharmacodynamics of GW395058, a Peptide Agonist of the Thrombopoietin Receptor, in the Dog, a Large-Animal Model of Chemotherapy-Induced Thrombocytopenia," *Stem Cells 18*: 360-365, 2000.

Dahlborg, S.A. et al., "The Potential for Complete and Durable Response in Nonglial Primary Brain Tumors in Children and Young Adults with Enhanced Chemotherapy Delivery," *The Cancer Journal from Scientific American 4*(2): 110-124, Mar./Apr. 1998.

Database BIOSIS, STN/CAS Online, Accession No. 2002: 129589, Doolittle et al., *Blood 98*(11, Part 1):37a-38a, Nov. 2001.

de Jong, R.S. et al., "Phase II Study of Intraperitoneal Cisplatin Plus Systemic Etoposide as Second-line Treatment in Patients With Small Volume Residual Ovarian Cancer," *European Journal of Cancer 31A*(5): 709-713, 1995.

Doolittle, N.D. et al., "Delayed Sodium Thiosulfate as an Otoprotectant Against Carboplatin-induced Hearing Loss in Patients with Malignant Brain Tumors," *Clinical Cancer Research 7*:493-500, Mar. 2001.

Einhorn and Loehrer, "Ifosfamide chemotherapy for pancreatic carcinoma," *Cancer Chemotherapy and Pharmacology 18*(Suppl. 2): S51-S54, 1986.

Harker, L.A. et al., "Prevention of Thrombocytopenia and Neutropenia in a Nonhuman Primate Model of Marrow Suppressive Chemotherapy by Combining Pegylated Recombinant Human Megakaryocyte Growth and Development Factor and Recombinant Human Granulocyte Colony-Stimulating Factor," *Blood 89*(1): 155-165, Jan. 1, 1997.

Howell, S.B. et al., "Intraperitoneal Cisplatin with Systemic Thiosulfate Protection," *Annals of Internal Medicine 97*(6): 845-851, Dec. 1982.

Isaacs, C. et al., "Randomized Placebo-Controlled Study of Recombinant Human Interleukin-11 to Prevent Chemotherapy-Induced Thrombocytopenia in Patients With Breast Cancer Receiving Dose-Intensive Cyclophosphamide and Doxorubicin," *Journal of Clinical Oncology 15*(11): 3368-3377, Nov. 1997.

Iwamoto, Y. et al., "'Two-Route Chemotherapy' Using High-Dose Ip Cisplatin and Iv Sodium Thiosulfate, Its Antidote, for Peritoneally Disseminated Cancer in Mice," *Cancer Treatment Reports 68*(11): 1367-1373, Nov. 1984.

Kim, S. et al., "Dose intensification of cisplatin chemotherapy through biweekly administration," *Annals of Oncology 4*: 221-227, 1993.

Muldoon, L.L. et al., "Delayed Administration of Sodium Thiosulfate in Animal Models Reduces Platinum Ototoxicity without Reduction of Antitumor Activity," *Clinical Cancer Research 6*:309-315, Jan. 2000.

Muldoon, L.L. et al., "Rescue from Enhanced Alkylator-Induced Cell Death with Low Molecular Weight Sulfur-Containing Chemoprotectants," *The Journal of Pharmacology and Experimental Therapeutics 296*(3): 797-805, 2001.

Neuwelt, E.A. et al., "First Evidence of Otoprotection Against Carboplatin-Induced Hearing Loss with a Two-Compartment System in Patients with Central Nervous System Malignancy Using Sodium Thiosulfate," *The Journal of Pharmacology and Experimental Therapeutics 286*(1): 77-84, 1998.

Neuwelt, E.A. et al., "In Vitro and Animal Studies of Sodium Thiosulfate as a Potential Chemoprotectant against Carboplatin-induced Ototoxicity," *Cancer Research 56*(4): 706-709, Feb. 15, 1996.

Neuwelt, E.A. et al., "Therapeutic Efficacy or Aortic Administration of N-Acetylcysteine as a Chemoprotectant against Bone Marrow Toxicity after Intracarotid Administration of Alkylators, with or without Glutathione Depletion in a Rat Model," *Cancer Research 61*:7868-7874, Nov. 1, 2001.

Piperno, E. et al., "Pathophysiology of Acetaminophen Overdosage Toxicity: Implication for Management," *Pediatrics 62*(5—Supplement): 880-889, Nov. 1978.

Robbins, K.T. et al., "Efficacy of Targeted Supradose Cisplatin and Concomitant Radiation Therapy for Advanced Head and Neck Cancer: The Memphis Experience," *International Journal of Radiation Oncology Biology Physics 38*(2): 263-271, May 1, 1997.

Vermeulen, N.P.E. et al., "Toxicity of fotemustine in rat hepatocytes and mechanism-based protection against it," *Chemico-Biological Interactions 110*:139-158, 1998.

Verschraagen, M. et al., "Pharmacokinetics and preliminary clinical data of the novel chemoprotectant BNP7787 and cisplatin and their metabolites," *Clinical Pharmacology & Therapeutics 74*(2): 157-169, Aug. 2003.

Wheeler, B.M. et al., "Ifosfamide in Refractory Male Germ Cell Tumors," *Journal of Clinical Oncology 4*(1): 28-34, Jan. 1986.

Iwamoto, et al., "*Inactivation of cis-diamminedichloroplatinum (II) in blood and protection of its toxicity by sodium thiosulfate in rabbits*," Cancer Chemother. Pharmacol. 15(3):pp228-32 (1985).

Kobayashi, et al., "*Therapeutic efficacy of two-route chemotherapy using cis-diamminedichloroplatinum(II) and its antidote, sodium thiosulfate, combined with the angiotensin-II-induced hypertension method in a rat uterine tumor*," Int. J. Cancer 47(6):pp893-8 (Apr. 1, 1991).

Markman, et al., "*Phase-1 trial of high-dose intravenous cisplatin with simultaneous intravenous sodium thiosulfate*," J Cancer Res Clin Oncol. 117(2):pp151-5 (1991).

Movsas, Benjamin, "*Innovative Treatment Strategies in Locally Advanced and/or Unresectable Non-Small Cell Lung Cancer*," J Moffitt Cancer Cntr (Jan./Feb. 2000).

Neuwelt, et al., "*First Evidence of Otoprotection Against Carboplatin-Induced Hearing Loss with a Two-Compartment System in Patients with Central Nervous System Malignancy Using Sodium Thiosulfate*," JPET 286:pp77-84 (1998).

Remsen, et al., "*Enhanced Delivery Improves the Efficacy of a Tumor—specific Doxorubicin Immunoconjugate in a Human Brain Tumor Xenograft Model*," Neurosurgery, vol. 46, No. 3 (Mar. 2000).

Robbins, et al., "*Phase I Study of Highly Selective Supradose Cisplatin Infusions for Advanced Head and Neck Cancer*," JClin Oncol. 12(10):pp2113-20 (Oct. 12, 1994).

Robbins, et al., "*Decadose' Effects of Cisplatin on Squamous Cell Carcinoma of the Upper Aerodigestive Tract. I. Histoculture Experiments*," Laryngoscope 106:pp37-42 (Jan. 1996).

Tepel, et al., "*Prevention of Radiographic-Contract-Agent-Induced Reductions of Renal Function by Acetylcysteine*," New Engl. J Med vol. 343, No. 3, pp180-184 (Jul. 20, 2000).

Trail, et al., "*Enhanced Antitumor Activity of Paclitaxel in Combination with the Anticarcinoma Immunoconjugate BR96-Doxorubicin*," Clin Cancer Res vol. 5:pp3632-3638 (Nov. 1999).

Treskes, et al., "*WR2721 as a modulator of cisplatin-and carboplatin-induced side effects in comparison with other chemoprotective agents: a molecular approach*," Cancer Chemother Pharmacol 33:pp93-106 (1993).

Uozumi, et al., "*Effectiveness of "Two-Route Chemotherapy" Using Cisplatin and Its Antidote, Sodium Thiosulfate, on Lifespan of Rats Bearing Metastatic Live Tumors*," Cancer Treat Rep 67(12):pp1067-1074 (Dec. 1983).

Yokoyama, et al., "*Superselective intra-arterial infusion chemotherapy of high-dose cisplatin for advanced paranasal sinus carcinomas*," Gan to Kagaku Ryoho 26(7): 967-973 (Jun. 1999) (Abstract).

\* cited by examiner

ADMINISTRATION OF A THIOL-BASED CHEMOPROTECTANT COMPOUND

RELATED APPLICATIONS

The present application claims priority to PCT/US01/40624 having an international filing date of Apr. 26, 2001 which claims the benefit of the filing dates under 35 U.S.C. § 119(e) to provisional U.S. patent application Ser. No. 60/199,936 filed on Apr. 26, 2000 and Provisional U.S. Ser. No. 60/229,870 filed on Aug. 30, 2000, which are hereby incorporated by reference.

FEDERALLY SPONSORED RESEARCH OR DEVELOPMENT

The present invention was partially supported under NIH grant No. NS33618 and by The Department of Veterans Affairs merit review grant. The United States Government may have certain rights in this invention.

BACKGROUND OF THE INVENTION

The present invention is based, in part, upon the discovery that a method of administration of N-acetylcysteine (NAC) markedly affects its effective biodistribution. The present invention provides a method for treating or mitigating the side effects, including organ damage, of cytotoxic cancer therapy for tumors located in the head or neck. Additionally, NAC or other thiols can be administered concurrently with, before or after, intra-arterial procedures and provides protective affects to prevent or diminish organ damage.

N-acetylcysteine (NAC) is an analog of cysteine. When NAC is administered to a mammal it is deacylated and enters a cellular synthetic pathway for the production of glutathione. Glutathione is involved in the cellular pathways influencing a tumor's resistivity to cytotoxic drugs. The cytotoxic properties of chemotherapeutic drugs can be enhanced by pretreatment with buthionine sulfoximine (BSO) thereby reducing intracellular glutathione. However, reduction of intracellular gluthionine will potentiate systemic toxicities associated with chemotherapeutic drugs. Thus, this procedure is dose-limiting. For protection, the glutathione levels of "normal" cells have to be reestablished if BSO is used to potentiate the cytotoxic properties of cytotoxic cancer therapies (Kamer et al., *Cancer Res.* 47:1593–1597, 1987; Ozols et al., *Biochem. Pharm.* 36:147–153, 1987; McLellan et al., *Carcinogenesis* 17:2099–2106, 1995; and Shattuck et al., *J. Parenteral Enteral Nutrition* 24:228–233, 1998). It may be possible to reduce the bone marrow toxicity of chemotherapeutic drugs by using sulfur-containing chemoprotective agents (thio, thiol, and thioether compounds) to mimic one or many of the activities of glutathione such as conjugation, free radical scavenging, and drug efflux via the multidrug resistance associated proteins. NAC and other thiol agents such as STS have early detoxifying activity not related to the later increase in glutathione levels. These early detoxifying effects occur because the thiols themselves mimic some actions of glutathione such as free radical scavenging, anti-oxidant activity, chemical conjugation, and activation of efflux pumps.

A potential problem with any chemoprotectant is the possibility of deactivating the anti-tumor effect of the chemotherapy or radiation therapy. The goal of chemoprotection is to reduce unwanted toxicities of chemotherapy or radiotherapy without affecting efficacy.

For brain tumor chemotherapy, one must attempt to increase the delivery of chemotherapy to the brain tumor and block the delivery of the chemoprotective agent. Additionally, one will want to target the chemoprotectant agent to the bone marrow to protect against myelosuppression and to liver, kidney and lung to prevent organ toxicity. Therefore, there is a need in the art to improve pharmacokinetics and biodistribution of chemoprotectant agents so that they will be more effective when delivered in a tissue-specific manner. Preferably, delivery is maximized to the bone marrow, chest and abdomen organs while minimized to the brain.

There are more than 10 specific active transport systems that transport compounds from the blood to the brain. Otherwise, substances, such as chemoprotectants can only nominally penetrate this barrier by passive diffusion. Brain tumors are particularly difficult to treat because the blood-brain barrier is an anatomical structure that limits the egress of constituents in the blood to the brain. Thus, brain tumors often respond poorly to chemotherapeutic drugs. There have been many attempts to try to increase brain bioavailability of various drug compounds to brain tissue. One technique uses osmotic BBB modification by administering mannitol through the internal carotid artery (Neuwelt et al., *Cancer Res.* 45:2827–2833, 1985). This technique is useful for administering the chemotherapeutic methotrexate to experimental brain tumors that would otherwise be inaccessible to this drug (it poorly crosses the BBB). The osmotic shrinkage caused by intracarotid mannitol administration allowed for temporary BBB disruption and increased tumor delivery of the methotrexate. Thus, a temporary disruption of the barrier functions of the BBB can be induced by a sugar, such as mannitol, and cause higher brain concentrations of a drug compound that would not otherwise have crossed the BBB. This BBB opening technique has also been investigated with other chemotherapeutic drugs (Neuwelt et al., *Proc. Natl. Acad. Sci. USA* 79:4420–4423, 1982; Fortin D. McCormich C I, Remsen L G, Nixon R, Neuwelt E A, "Unexpected neurotoxicity of etoposide phosphate when given in combination with other chemotherapeutic agents after blood-brain barrier modification using propofol for general anesthesia in a rat model," *Neurosurgery* 47:199–207, 2000).

An example of chemoprotection is a drug neutralization technique described in U.S. Pat. No. 5,124,146 wherein excess toxic drug compounds are "mopped up" or bound by a binding or neutralizing agent not able to penetrate the blood brain barrier. This technique requires precise timing as to when the drug neutralizing agent is administered.

There are several thiol-based chemoprotectant agents that contain a thio, thiol, aminothiol or thioester moiety. Several thiol-based chemoprotectant agents have been shown to provide protection against at least some of the systemic toxicities caused by alkylating chemotherapeutics. The thiol based chemoprotective agents include N-acetyl cysteine (NAC), sodium thiosulfate (STS), GSH ethyl ester, D-methionine, and thiol amifostine (Ethyol or WR2721). NAC is currently marketed in the United States under an orphan indication for oral and intravenous (i.v.) administration for overdosing with acetaminophen. NAC has also been shown to be a chemoprotectant when administered in combination with a vanadate compound (U.S. Pat. No. 5,843,481; and Yarbo (ed) *Semin. Oncol.* 10 [Suppl 1]56–61, 1983). Ethyol is also marketed in the United States under the generic name of Amifostine. GSH ethyl ester is an experimental thiol not yet marketed for clinical use, but is representative of the class of thiols that is converted directly to glutathione.

In addition, NAC has been shown to be a mucoregulatory drug used for the treatment of chronic bronchitis (Grassi and Morandini, *Eur. J. Clin. Pharmacol.* 9:393–396, 1976; Multicenter Study Group, *Eur. J. Respir. Dis.* 61: [Suppl.] 93–108, 1980; and Borman et al., *Eur. J. Respir. Dis.* 64:405–415, 1983).

In plasma, NAC can be present in its intact, reduced forms as well as in various oxidized forms. It can be oxidized to a disulfide by reacting with other low molecular weight thiols, such as cysteine and glutathione. NAC can be oxidized by reacting the thiol groups of plasma proteins. When administered intravenously, the brain levels of NAC are <5%. Yet, NAC does cross the BBB if given by an intra-arterial route of administration. NAC is rapidly cleared from plasma via the liver and kidney. Moreover, NAC does not show neurotoxic properties.

There are bioanalytical methods for the determination of NAC in plasma, including Cotgreave and Moldeus, *Biopharm. Drug Disp.* 8:365–375, 1987; and Johansson and Westerlund, *J. Chromatogr.* 385:343–356, 1986 that also permit a determination of other forms of NAC. Moreover, cysteine and cystine have been identified as major metabolites of NAC. The excreted urinary product is inorganic sulfate together with small amounts of taurine and unchanged NAC. According to the label indications for NAC manufactured by (American Regent Laboratories Shirley, N.Y.), vials of NAC are produced as a sterile solution for oral administration diluted with water or soft drinks.

Another thiol-containing chemoprotectant is sodium thiosulfate (STS). Its chemical formula is $Na_2S_2O_3$ and it has been used clinically for cyanide poisoning and for nephrotoxicitiy caused by cisplatin. STS is cleared rapidly from circulation primarily by the kidney. The plasma half life after a bolus injection is about 17 minutes. STS can also inactivate platinum agents through covalent binding to platinum agents at a molar excess >40:1 (STS:platinum). With i.v. administration of STS, the brain levels of STS are <5% of blood showing poor brain localization. Neurotoxic side effects, in the form of seizures, may occur when brain levels of STS are enhanced through i.a. administration within 30 min of BBB disruption.

Diagnostic or therapeutic procedures involving intra-arterial catheterization can cause a variety of organ toxicities, complications and side effects from injuries. For example, placement of an arterial catheter can dislodge plaques from artery walls that can lodge elsewhere in the vasculature causing ischemia. Ischemia increases the presence of free radicals and leads to cell death. As another example, nephrotoxicity of radiographic contrast agents can lead to acute renal failure even when measures are taken to reduce toxic effects. As a third example, intra-arterial catheterization is used during angioplasty procedures wherein a balloon catheter is inserted into the arterial circulation and then threaded (with radiographic contrast agents for visualization) to a site of occlusion. In dilating the occluded artery, various forms of tissue damage and inflammatory reactions (e.g., restenosis) can occur including ischemic tissue injury.

Specifically, toxic side effects of intra-arterial catheterization and infusion of radiographic contrast agents prolong hospital stays, add to the cost of medical care, and can be fatal. The incidence of radiographic-contrast-agent-induced acute renal failure, currently estimated to be as high as 50 percent among patients with diabetes mellitus and preexisting renal disease who receive contrast agents, is likely to remain high as the use of invasive intra-arterial procedures to diagnose and treat complex disease continues to grow.

Radiographic contrast agents are used in medical imaging. Medical imaging is the production of images of internal organs and tissues by the application of nonsurgical techniques. Contrast agents are chemicals used to enhance the image, and to increase contrast between the target organ and surrounding tissues. Prevention or mitigation of renal failure after the administration of a radiographic contrast agent has been notably difficult. Calcium-channel antagonists, adenosine antagonists, and dopamine have all been used without convincing evidence of benefit.

Tepel et al. proposed the oral administration of approximately 1200 mg of N-acetylcysteine per day, given orally in divided doses on the day before and on the day of the administration of the radiographic contrast agent. (Tepel et al., *New England J. Med.*, Jul. 20, 2000). Oral administration allegedly prevented the expected decline in renal function in all patients with moderate renal insufficiency, and therefore high risk, who were undergoing computed tomography.

NAC has been used successfully to ameliorate the toxic effects of a variety of experimentally or clinically induced ischemia-reperfusion syndromes of the heart, kidney, lung, and liver. In each of these syndromes, it is thought that the activity of NAC is related to its action as a free-radical scavenger, or as a reactive sulphydryl compound that increases the reducing capacity of the cell. The specific mechanism of NAC to prevent the nephrotoxic effects of contrast agents is not known.

Therefore, there is a need in the art to find better ways to use thiol-based chemoprotectants, such as NAC and STS and to take advantage of their pharmacokinetic properties. There is also a need in the art to find better, higher dose cytotoxic treatment regimens for head and neck as well as brain tumors that avoid dose-limiting due to side effects.

There is a need in the art for a compound that can be used with intra-arterial catheterization procedures to reduce organ toxicity. Diabetic patients with markedly reduced renal function, in whom coronary angiography is often delayed because of the considerable risks to renal function entailed by angiography, may particularly be benefited by targeted delivery of a protectant agent. Additionally, there is a need in the art for a low cost compound which is generally available, easy to administer and has limited side effects. There is a need in the art for a compound and a method of administration of the compound that can be used to reduce or eliminate tissue damage caused by intra-arterial procedures.

Additionally, there is a need in the art to find better ways to use thiol-based radiographic protectants, such as NAC and STS (sodium thiosulfate) and to take advantage of their pharmacokinetic properties. There is also a need in the art to find an agent protective against intra-arterial catheterization-induced reductions in organ function. These and other problems of the prior art are solved by the present method and pharmaceutical composition.

SUMMARY OF THE INVENTION

The present invention provides a method and compound for locally administering a thiol based chemoprotectant to treat or mitigate the side effects of cytotoxic cancer therapy for brain tumors located in the head or neck. Further, the present invention provides a method and compound for locally administering a thiol-based chemoprotectant to an organ or tissue to protect against injury from diagnostic or therapeutic intra-arterial procedures. The method includes administering a thiol-based chemoprotectant agent intra-arterially in conjunction with, before, or after administration of a cytotoxic agent.

In one embodiment, the cytotoxic agent is a cancer chemotherapeutic agent. The cytotoxic agent is dose-limited due to myelosuppressive effects systemically. The cancer chemotherapeutic agent is selected from the group consisting of cis-platinum compounds, taxanes (e.g., paclitaxel), steroid derivatives, anti-metabolites, vinca alkaloids, adriamycin and doxorubicin, etoposide, arsenic derivatives, intercalating agents, alkylating agents (such as melphalan) and combinations thereof. The cytotoxic agent is administered within eight hours (before, during or after) of the thiol-based chemoprotectant agent administration. In yet another embodiment, when the tumor is located in the head or neck or brain, the cytotoxic agent is administered such that the majority of the dose is directed to the head or neck region.

Preferably, the thiol-based chemoprotectant agent is a compound selected from the group consisting of N-acetyl cysteine (NAC), sodium thiosulfate (STS), GSH ethyl ester, D-methionine, Ethyol, and combinations thereof. In one embodiment, the thiol-based chemoprotectant agent is administered in a pyrogen-free sterile solution by a catheterization procedure via a catheter having a tip that is located in the descending aorta. In yet another embodiment, the dose of the thiol-based chemoprotectant agent per procedure is from about 200 mg/m$^2$ to about 40 g/m$^2$. Most preferably, the dose of NAC agent per procedure is from about 400 mg/m$^2$ to about 1200 mg/m$^2$ and the dose of STS is from about 5 g/m$^2$ to about 40 g/m$^2$.

In one embodiment, the intra-arterial catheter is positioned in an artery providing blood flow to a potential site or organ of injury. In yet another embodiment, the intra-arterial administration is at a site in the descending aorta. In yet another embodiment, the injury is caused by injecting a cytotoxic agent including a radiographic contrast agent using an intra-arterial catheter.

In yet another embodiment, the thiol-based chemoprotectant agent is administered in a pyrogen-free, non-oxidized sterile solution having a reducing agent, a buffer to maintain pH at or near physiologic pH and a metal chelating agent to bind metal ions that can catalyze oxidation of the thiol-based chemoprotectant agent. Preferably, the reducing agent is selected from the group consisting of vitamin E, tocopherol, dithiothreitol, mercaptoethanol, glutathione, and combinations thereof. Preferably, the buffer is one that is relatively non-toxic and can maintain a pH of between 6 and 8 (e.g., phosphate buffer, Tris buffer). Preferably, the thiol-based chemoprotectant agent is stored in a vial having a blanket of an inert gas. Most preferably, the inert gas is selected from the group consisting of argon, helium, nitrogen and mixtures thereof.

The present invention further provides a pharmaceutical composition for treatment to protect against injury from diagnostic or therapeutic intra-arterial procedures, and for head and neck brain tumors. The compound includes a first agent for intra-arterial administration and a second agent administered intra-arterially.

Preferably the second agent is a thiol-based chemoprotectant agent. In one embodiment, the second agent is administered to the descending aorta or further downstream.

The first agent is administered to a carotid or vertebral artery. The first agent is a radiographic contrast agent delivered intra-arterially to position a catheter. In one embodiment, the first agent is administered within eight hours (before, during or after) of the second agent. The second agent is administered immediately after intra-arterial catheterization, prior to radiographic contrast agent, to within eight hours of the radiographic contrast agent.

In one embodiment, the second agent is administered in a pyrogen-free, sterile solution. In further embodiments, the solution is non-oxidized and has a reducing agent, a buffer to maintain pH at or near physiologic pH and a metal chelating agent to bind up metal ions that can catalyze oxidation of the thiol-based chemoprotectant agent. Preferably, the reducing agent is selected from the group consisting of vitamin E, tocopherol, dithiothreitol, mercaptoethanol, glutathione, and combinations thereof. Preferably, the buffer is one that is relatively non-toxic and can maintain a pH of between 6 and 8 (e.g., phosphate buffer, Tris buffer).

In one embodiment, the thiol-based chemoprotectant agent is stored in a vial having a blanket of an inert gas. Most preferably, the inert gas is selected from the group consisting of argon, helium, nitrogen and mixtures thereof. Preferably, the thiol-based chemoprotectant agent is a compound selected from the group consisting of N-acetyl cysteine (NAC), sodium thiosulfate (STS), GSH ethyl ester, D-methionine, Ethyol, and combinations thereof. Preferably, the dose of the thiol-based chemoprotectant agent per procedure is in the range of 200 mg/m$^2$ to 2000 mg/m$^2$. In a further preferred embodiment, the dose of NAC per procedure is in the range of 400 mg/m$^2$ to 1200 mg/m$^2$.

Further, one advantage of NAC is that it is protective against multiple intra-arterial procedure toxicities, including but not limited to those caused by radiographic contrast agents.

The methods and compounds will best be understood by reference to the following detailed description of the preferred embodiment, taken in conjunction with the accompanying drawings. The discussion below is descriptive, illustrative and exemplary and is not to be taken as limiting the scope defined by any appended claims.

BRIEF DESCRIPTION OF THE DRAWINGS

FIG. 4A shows the effect of BSO and N-acetylcysteine on Carboplatin cytotoxicity. FIG. 4B shows the effect of BSO and N-acetylcysteine on etoposide phosphate cytotoxicity. Cytotoxicity was assessed in cultured LX-1 SCLC cells, 1×10$^4$ cells per well in 96 well plates, using the WST colorometric assay. BSO cytoenhancement consisted of preincubation at 100 µM BSO for 18 hours. The chemoprotective agent was added immediately after chemotherapy. The experimental conditions were dose/responses for chemotherapy (carboplatin or etoposide phosphate) alone (m), BSO cytoenhancement (▲), N-acetylcysteine rescue, (1000 μg/ml N-acetylcysteine, n), or BSO cytoenhancement and N-acetylcysteine rescue (u). Data are expressed as the percentage of live cells compared to untreated control samples without chemotherapy and each point represents the mean±standard deviation of 4 wells.

FIG. 7A shows caspase-2 enzymatic activity. FIG. 7B shows TUNEL staining for DNA fragmentation. Apoptosis was assessed in cultured LX-1 SCLC cells pretreated for 18 hours with or without 100 μM BSO. The experimental conditions were no addition (open bars), melphalan (10 μg/ml, striped bars) or melphalan (10 μg/ml) plus N-acetylcysteine (1000 μg/ml) (cross hatched bars) for 20 h prior to harvest. Caspase-2 activity is expressed as percentage activity in untreated control samples (mean±standard deviation, n=3). TUNEL staining is expressed as the percentage of cells showing positive staining.

In FIG. 10B and FIG. 10D animals received BSO (10 mg/kg i.p.×3 d) prior to treatment with chemotherapy. Panel A shows granulocyte counts without BSO FIG. 10B shows granulocyte counts with BSO (mean+/−SEM, n=6 per group) FIG. 10C shows platlet count without BSO FIG. 10D shows platlet count with BSO. Significant difference from the no protectant groups were determined by Wilcoxon/ Kruskal-Walliis rank sums tests (*p<0.05, **p<0.01).

DETAILED DESCRIPTION OF THE INVENTION

Figure 1:
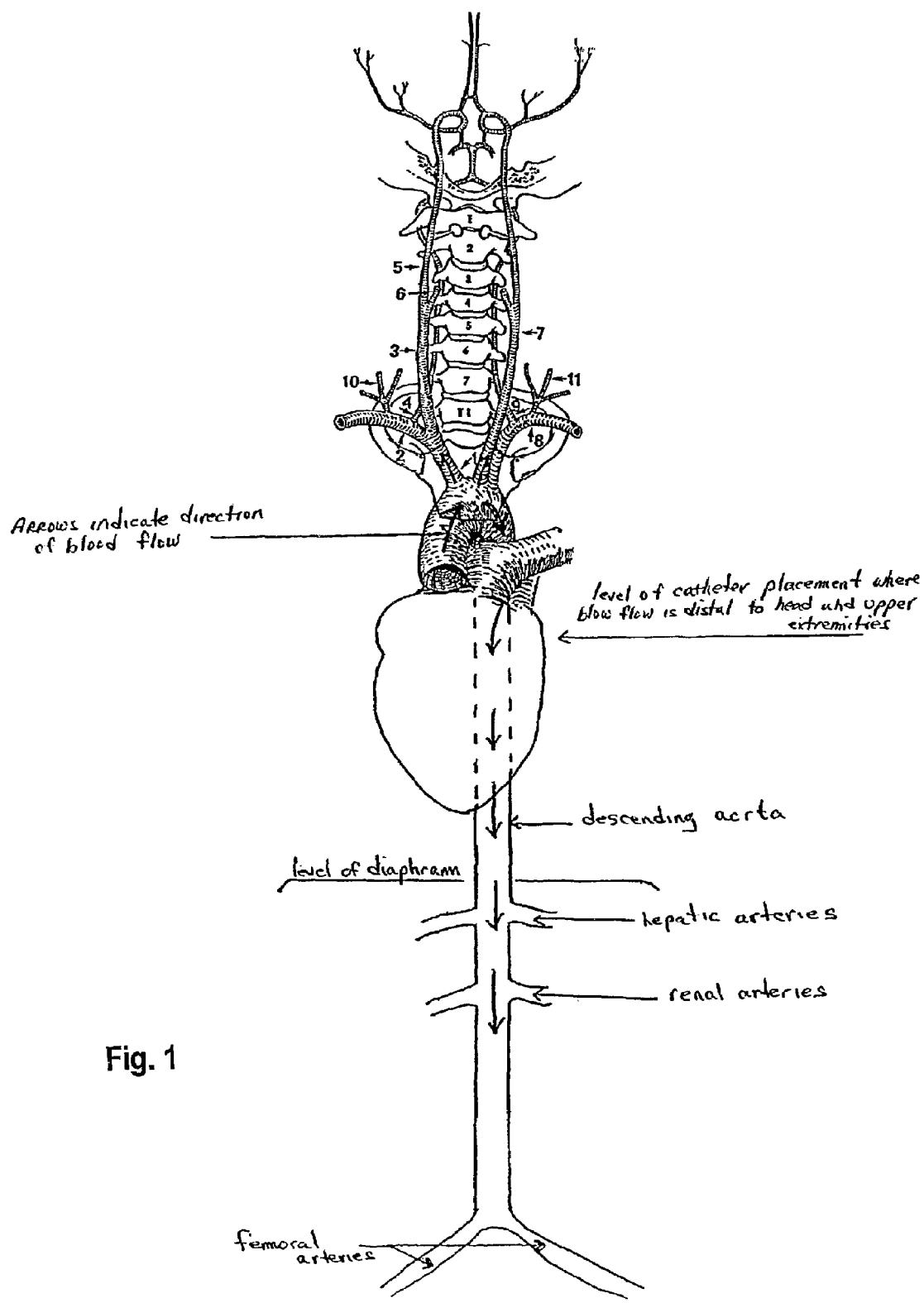
FIG. 1 shows an anatomical diagram of major arteries and the top level for placing the catheter for administration of the thiol-based chemoprotectant agent.

The present method includes administration of at least two different agents for treating brain or head and neck tumors. The first agent is a cytotoxic agent. In one example, the cytotoxic agent is radiation or a chemotherapeutic agent. The radiation or chemotherapeutic agent generally has a dose-limiting systemic side effect of myelosuppression. If myelosuppression is too severe, it is life threatening as the patient is unable to generate enough white blood cells of multiple lineages to coordinate immune surveillance function for defending against pathogen attack. Therefore, any ability to reduce bone marrow toxicity or myelosuppression will allow for greater and more effective administration of the cytotoxic agent.

Current treatment to reduce bone marrow side effects include recombinant growth factors that are lineage-specific. Such growth factors have included EPO (erythropoietin) for red cells and G-CSF (granulocyte colony stimulating factor) or GM-CSF (granulocyte macrophage colony stimulating factor) for various lineages of infection-fighting white cells. In addition, TPO (thrombopoietin) is in clinical trials for augmenting a platelet response in myelosuppressed patients. However, such growth factors act to stimulate lineage specific precursor cells to divide and mature down lineage-specific paths. Thus, the use of growth factors results in a more rapid recovery from bone marrow toxicity but does not generally reduce the nadir of toxicity. Such growth factors have been able to allow a patient to tolerate a greater number of cytotoxic treatments (where myelosuppression is a limiting toxicity), but generally not higher doses of the cytotoxic agent administered.

The method allows for greater doses of the cytotoxic agent directed to head and neck tumors. Specifically, the cytotoxic agent (if it is a chemical compound or combination of compounds) is administered intra-arterially such that it is directed initially to the head and neck circulation. Thus, the highest concentration of cytotoxic agent is direct to the location of the tumor to be treated. By contrast, iv administration provides for the same concentration of cytotoxic agent in the bone marrow, where side effects happen, as systemic dose.

Thiol-based chemoprotectant agents are nonspecific chemoprotectant agents. They are not specific to "normal" tissue or cells but can protect both normal and tumor tissue. Earlier attempts to utilize the chemoprotectant properties of thiol-based chemoprotectant agents have failed due to the fact that they were administered either orally or systemically, they were rapidly metabolized, and protected both normal and tumor tissue. Systemic administration includes iv.

The method includes utilizing a spatial two-compartment pharmacokinetic model which results in a general tissue first pass effect to prevent significant or chemoprotectant doses of thiol-based chemoprotectant agents from gaining general systemic circulation through the venous circulatory system. The method utilizes only one pass going to tissues below the level of the heart in order to effect a chemoprotectant effect. Therefore, head and neck tumors are treatable through regionalization of doses of the cytotoxic agent to the brain or head and neck where the tumor tissue is located and doses of the chemoprotectant to general tissues below the level of the heart where the majority of bone marrow tissue is located.

The ability of a thiol-based chemoprotectant agent to show a first pass effect through non-liver tissue was surprising. Once any thiol-based chemoprotectant agent that is not tissue-absorbed gains access to the venous circulation, it will be cleared through a liver first pass or rapidly removed through renal clearance. When administered not according to the method described, NAC is actively transported across the BBB. An example of spatial compartmentalization is the administration of a thiol-based chemoprotectant agent into the descending aorta or lower preventing any significant chemoprotectant concentrations of the thiol-based chemoprotectant agent from ever reaching the brain or head or neck region where the tumor tissue is located. Spatial compartmentalization is facilitated by the rapid tissue uptake of the thiol-based chemoprotectant agent. Spatial compartmentalization is needed in order to achieve any meaningful therapeutic benefit with a thiol-based chemoprotectant agent. Without spatial compartmentalization, the undesirable result of the thiol-based chemoprotectant agent protecting the tumor tissue will occur. In the case of NAC as the thiol-based chemoprotectant agent, passage of the BBB by NAC will restore glutathione levels to the brain tumor, thereby increasing the tumor's resistance to cytotoxic drugs.

The ability to set up a two-compartment pharmacokinetic model was discovered through a series of experiments using in vitro and in vivo models and administering both chemotherapeutic agents and the thiol-based chemoprotectant agents NAC and STS. However, it should be noted that radiation therapy can be similarly localized or even more easily localized than chemotherapeutic agents. Tissue culture pharmacological studies have shown that treatment with NAC and STS can reduce cell killing by the chemotherapeutics melphalan, carboplatin, and cisplatin. The in vivo results show that localized NAC or STS administration resulted in less myelosuppression and faster recovery from chemotherapy. Moreover, synergistic results were observed with the combination of thiol-based chemoprotectant agent NAC and STS providing evidence for a combination of thiol-based chemoprotectant agents to enhance the protective role when the combination of thiol-based chemoprotectant agents is administered according to the inventive process.

As shown in FIG. 1, in another embodiment of the method, a thiol-based chemoprotectant agent is administered intra-arterially such that it is directed systemically. This provides the highest concentration of thiol-based chemoprotectant agent to the location of organ damage, for example the kidneys, to protect against reduction of renal function. Oral administration, by contrast, provides for general systemic administration with the concentration of protective agent going elsewhere in the body, mainly the liver, and requiring higher dosages so as to provide a sufficient dose at the kidney (often the site of organ damage for radiographic contrast agents). In addition, the thiol-based chemoprotectant agent is not specific to normal tissue or cells but can protect both normal and tumor tissue.

The method is based upon results obtained utilizing a spatial two-compartment pharmacokinetic model that resulted in a general tissue first pass effect to prevent significant or radiographic-protectant doses of thiol-based radiographic-protectant agents (specifically illustrated are NAC and STS) from gaining general systemic circulation through the venous circulatory system. Thus, there was a surprising need for only one pass going to tissues of the renal system. This result prevented decreased renal function through regionalization of doses of the radiographic agent to the area where radiography is to be performed and doses of the protectant to the renal system.

As shown in FIG. 1, a catheter was inserted into the circulatory system generally via the femoral artery. In the first embodiment, a catheter is inserted into the body and administers a dosage of radiographic contrast agent into the body. An effective dosage of the thiol-based protective agent, preferably NAC, is administered at any time from immediately after the intra-arterial catheterization, preferably before contrast agent, to within about eight (8) hours after the administration of the radiographic contrast agent. The catheter for delivery of the radiographic protective agent is preferably inserted into the arterial system downstream of the aorta and directed in the mesenteric artery system. The thiol-based protective agent is introduced into the body at any time within about 5 hours after administration of the radiographic contrast agent to reduce or eliminate renal failure or decrease in renal function associated with administration of a renal contrast agent.

In a further embodiment, a catheter is inserted into the circulatory system (e.g., femoral artery) and administers an effective dosage of a thiol-based protective agent into the body. A radiographic contrast agent is administered by the same catheter and is used to position the catheter to the appropriate place for the therapeutic or diagnostic procedure. The thiol-based protective agent is introduced into the body, generally via the same arterial catheter, at any time within about 5 hours before or after administration of the radiographic contrast agent. Preferably, the thiol-based protective is administered via the arterial catheter one or a plurality of times during the procedure.

Pharmaceutical Formulations

Techniques for the formulation and administration of the compounds of the instant application may be found in "Remington's Pharmaceutical Sciences" Mack Publishing Co., Easton, Pa., latest addition. Suitable routes of administration are intra-arterial.

The compositions and compounds of the present invention may be manufactured in a manner that is itself known, e.g., by means of conventional mixing, dissolving, emulsifying, encapsulating, entrapping, or lyophilizing processes. Pharmaceutical compositions for use in accordance with the present invention thus may be formulated in conventional manner using one or more physiologically acceptable carriers comprising excipients and auxiliaries that facilitate processing of the active compounds into preparations, which can be used pharmaceutically. Proper formulation is dependent upon the route of administration chosen.

For injection, the compounds of the invention may be formulated in aqueous solutions, preferably in physiologically compatible buffers, such as Hank's solution, Ringer's solution, or physiological saline buffer. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulary agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g., sterile pyrogen-free water, before use. In one embodiment, a reducing agent or an anti-oxidant agent is added to the formulation of the thiol-based protective agent to prevent oxidation of the thiol-based protective agent. The antioxidant may include, but is not limited to, vitamin E, tocopherol, dithiotreitol, mercaptoethanol, glutathione. In one embodiment, an inert or non-oxidizing gas is added to a vial for intra-arterial administration. Examples of such gasses are nitrogen, argon, helium, and combinations/mixtures thereof.

A therapeutically effective dose refers to that amount of the compound that results in a reduction in the development or severity of myelosuppression. In another embodiment, toxicity and therapeutic efficacy of such compounds can be determined by standard pharmaceutical, pharmacological, and toxicological procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from cell culture assays or animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1).

The amount of composition administered will, of course, be dependent on the subject being treated, on the subject's weight, the severity of the affliction, the manner of administration and the judgment of the prescribing physician.

According to the method, a thiol-based chemoprotectant agent is administered intra-arterially in order for systemic tissues to be exposed to an initial dose of the thiol-based chemoprotectant agent in high enough concentration to provide a chemoprotective effect and to bypass the venous circulation and be eliminated by the liver. NAC is actively transported across the BBB. In one embodiment, to prevent access to the brain, after a transfemoral carotid/vertebral artery catheter is placed to perfuse the brain, the catheter can then be subsequently retracted and placed in the descending aorta for NAC infusion, thus performing a single surgical procedure with one catheter. This allows for minimal risk from arterial catheter procedures only and for high concentrations of NAC to be delivered to peripheral tissues and organs but not to brain and head.

Synthesis

Each thiol-based chemoprotectant agent, such as NAC or STS, can be synthesized by convention methods and are commercially available as a sterile solution.

EXAMPLE 1

This example shows the results of an in vivo experiment in rats having a catheter implanted in the descending aorta for NAC administration. The rats were set up for drug administration by pushing a catheter forward past the junction of the external and internal carotid arteries (toward the aorta), and temporarily sealing off the internal carotid for good measure so nothing goes to the brain (left carotid aortic infusion method). In patients where entry is via the femoral artery and the catheter is threaded through the aorta to get to the brain in the first place, one would just pull the catheter back to the aorta to do the NAC infusion.

Rats were treated with carboplatin (200 mg/m$^2$), melphalan (10 mg/m$^2$) and etoposide phosphate (100 mg/m$^2$). In the NAC animals, NAC was infused with the left carotid aortic infusion method immediately after the chemotherapeutic agents, at concentrations ranging from 400–1200 mg/M$^2$. White blood cells (wbc) and platelets (plt) were counted at baseline before the experiment and at 6 and 9–11 days after treatment with the chemotherapeutic agents. The animals that did not receive NAC were tested on day 9–10 while the NAC animals were tested on day 10–11. Counts are in 1000s per µl blood. These data in the initial experiment shown in Table 1 provide initial results without a white blood cell effect. The lack of white blood cell effect was not repeated as there were significant effects shown below.

TABLE 1

| chemo alone | wbc base | wbc d6 | wbc d9/10 | plt base | plt d6 | plt d9/10 |
|---|---|---|---|---|---|---|
| mean | 11.4 | 0.8 | 3.2 | 778 | 63 | 164 |
| +/−sd | +/−4.1 | +/−0.2 | +/−1.6 | +/−233 | +/−59 | +/−91 |
| number | 8 | 4 | 3 | 7 | 4 | 3 |
| chem + NAC | wbc base | wbc d6 | wbc d10/11 | plt base | plt d6 | plt d10/11 |
| mean | 7.9 | 0.5 | 4.8 | 817 | 101 | 1232** |
| +/−sd | +/−2.1 | +/−0.2 | +/−0.7 | +/−142 | +/−48 | +/−167 |
| number | 5 | 4 | 3 | 5 | 4 | 3 |

The data in table 2 show additional results. In the NAC animals, NAC was infused by the left carotid aortic infusion method 30 min prior to chemo, at a concentration of 1200 mb/m2. White blood cells (wbc) and platelets (plt) were counted at baseline before the experiment and at 6 and 9 days after treatment with the chemotherapeutic agents. The data in Table 1 show that NAC treatment decreased the nadir blood count for both white cells and platelets, and blood counts recovered from chemotherapy faster.

TABLE 2

|  | wbc base | wbc d6 | wbc d9 | plt base | plt d6 | plt d9 |
|---|---|---|---|---|---|---|
| chemo alone | | | | | | |
| mean | 6.4 | 1.6 | 5.2 | 878 | 187 | 599 |
| +/−sd | +/−0.3 | +/−0.4 | +/−0.7 | +/−46 | +/−70 | +/−187 |
| number | 6 | 6 | 6 | 6 | 6 | 6 |
| chem + NAC | | | | | | |
| mean | 5.1 | 3.3 | 6.2 | 721 | 388 | 1155 |
| +/−sd | +/−0.4 | +/−0.7 | +/−1.6 | +/−59 | +/−95 | +/−154 |
| number | 6 | 6 | 6 | 6 | 6 | 6 |

These data show that with NAC the platelets recovered from chemotherapy faster.

Figure 2A:
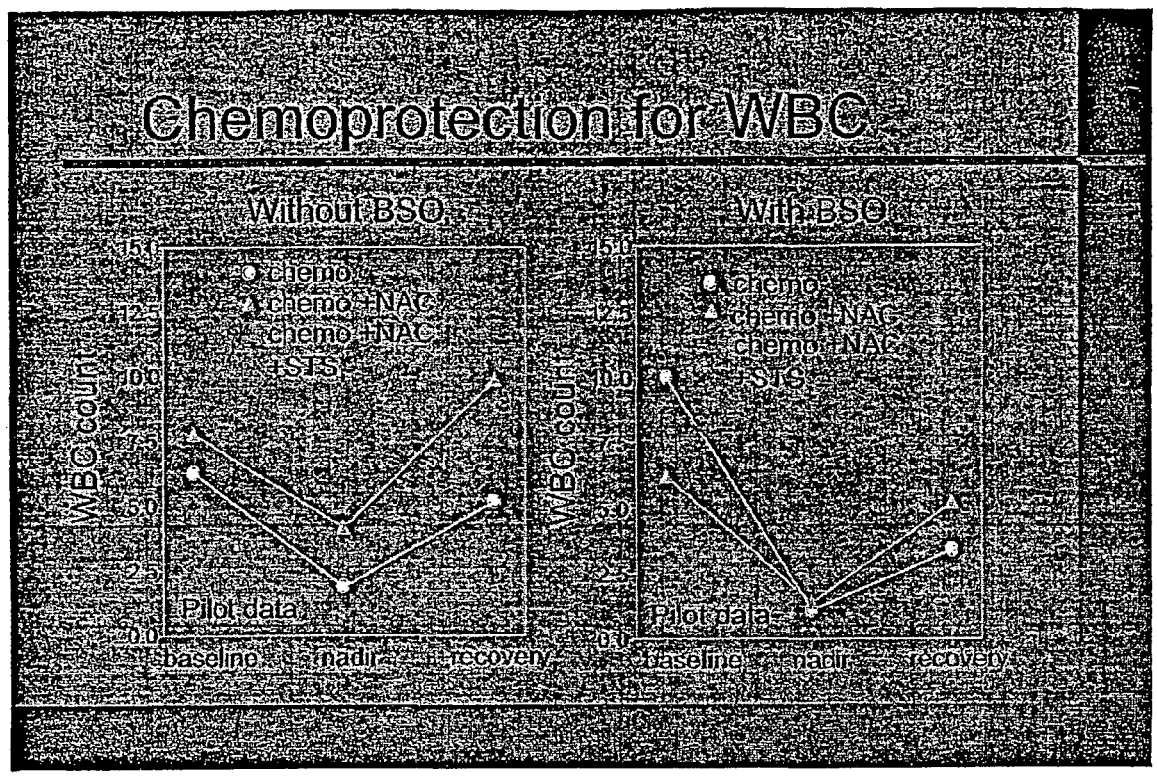
FIG. 2A shows the effect on white blood cells, FIG. 2B the effect on platelets and FIG. 2C the effect on granulocytes.
Figure 2B:
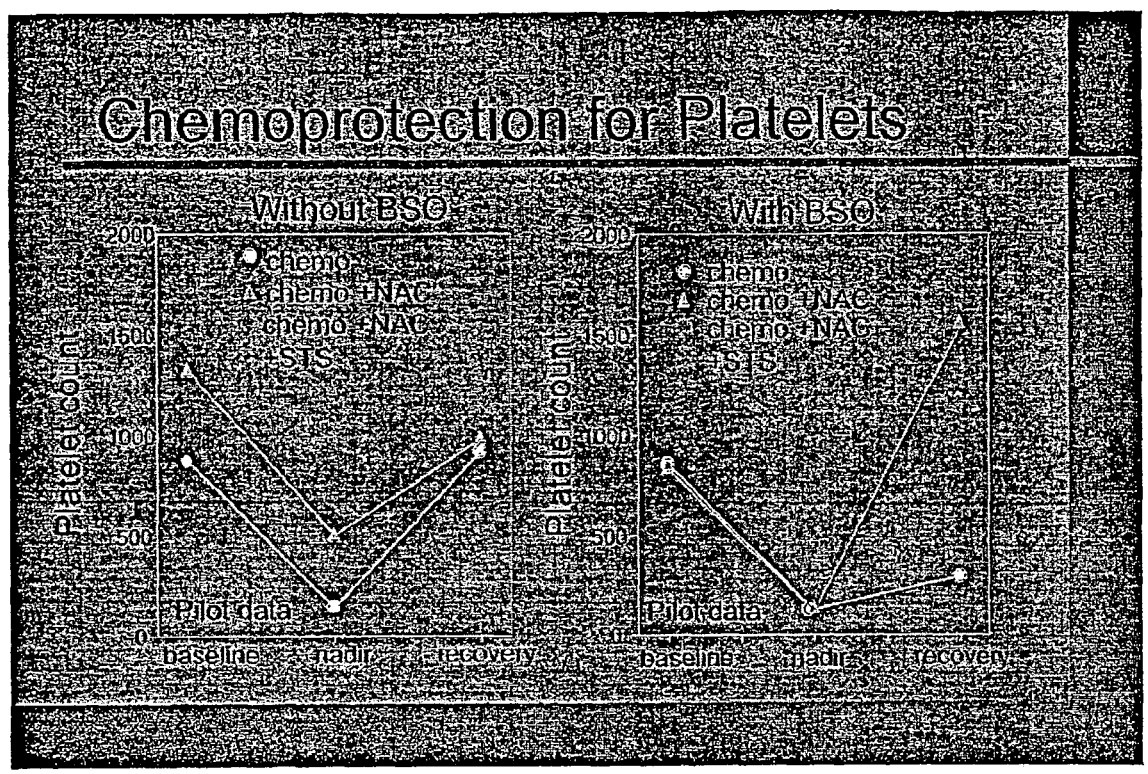
FIGS. 2(A–C) shows the effect of bone marrow recovery and lower nadirs using the left carotid aortic infusion inventive method with chemotherapy and the chemoprotectant NAC. Specifically.
Figure 2C:
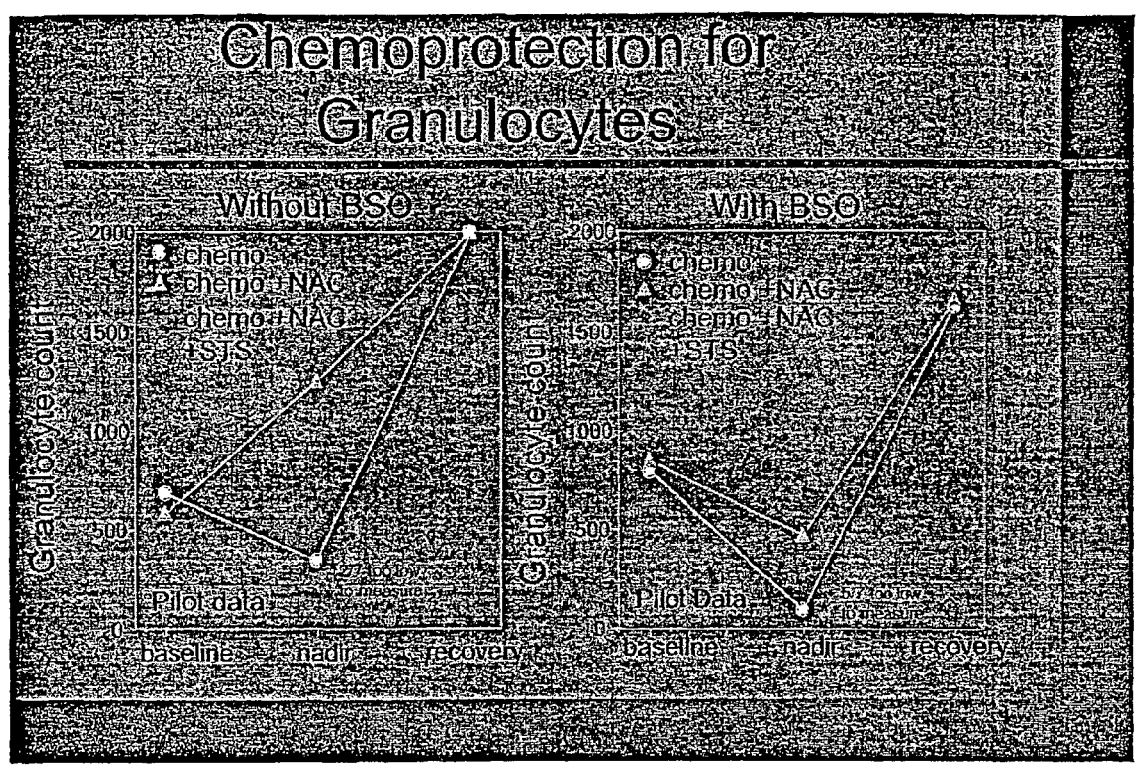

In addition, the experiment with the same chemotherapy agents at the same doses with and without BSO (buthionine sulfoximine) shows improved white blood cell recovery and higher nadirs with the chemoprotectant (NAC alone or with STS at the doses listed above) in FIG. 2A. Similar data are shown with platelets in FIG. 2B, and with granulocytes in FIG. 2C.

EXAMPLE 2

This example shows the results of NAC delivery by different means of catheter-based administration. In this experiment, radiolabeled NAC was administered to rats by three different routes. Liver and kidney tissue, in addition to the ipsilateral and contralateral hemispheres of the brain, were analyzed for radioactivity. Results are shown as the percent of the injected radioactive dose per gram of tissue. Route indicates intravenous (i.v.), intra-arterial into the right carotid artery (i.a.), or left carotid with internal artery occlusion and aortic infusion (left carotid aortic infusion). The left carotid aortic infusion intra-arterial method uses descending aorta placement of the catheter tip and NAC administration.

| route | left hem | right hem | liver | kidney | number |
|---|---|---|---|---|---|
| i.v. | 0.02 | 0.03 | 0.59 | 0.72 | 2 |
| i.a. | 0.03 | 0.41 | 0.57 | 0.70 | 3 |
| Left carotid aortic infusion | 0.04 | 0.04 | 0.29 | 1.42 | 2 |

These data show that i.a. delivery provided much brain delivery in the infused hemisphere. When the NAC was administered i.v., negligible amounts were found in brain (0.03% of the injected dose, n=2). When radiolabeled NAC was administered intraarterially into the right carotid artery of the rat, high levels of radiolabel were found throughout the right cerebral hemisphere. Delivery was 0.41% of the injected dose (n=3), comparable to the levels found in liver (0.57% of the injected dose) or kidney (0.70% of the injected dose). In contrast, the left carotid aortic infusion method prevented brain delivery. The Left carotid aortic infusion method also changed bio-distribution in peripheral tissues in that liver delivery was decreased and kidney delivery was increased. The change in tissue delivery with different modes of administration is likely due to NAC being related to the amino acid cysteine that is rapidly bound by tissues via the amino acid transporters. In summary, the method of administration of NAC markedly affected its biodistribution.

EXAMPLE 3

This example tested whether the inventive method for intra-arterial infusion (via the left carotid artery, with left internal artery occlusion) could reduce brain delivery of NAC and increase systemic delivery. Brain delivery was 0.04% of the injected dose with the inventive method (n=2).

In conjunction with other pharmacological and physiological data, these results show that NAC is protective when N-acetylcysteine is administered prior to, (preferably 30 minutes prior to), the cytotoxic agent at a dose which provides a serum concentration of NAC of between 0.5 mM to 15.0 mM, preferably 5 mM to 12.5 mM. Generally, a dose of between 40.0 mg/kg to 1000 mg/Kg of N-acetylcysteine will provide an appropriate serum concentration in humans and other mammals.

EXAMPLE 4

This example shows the inventive process being used to compare bone marrow toxicity of a chemotherapeutic agent (alone or in combination) to administration of NAC alone (1000–1200 mg/m$^2$ alone or in combination) and NAC plus STS. The chemotherapy agents were carboplatin (200 mg/m$^2$) melphalan (10 mg/m$^2$) and etoposide phosphate (100 mg/m$^2$). The dose of STS in the rat was 8 g/m$^2$ that is the equivalent to 20 g/m$^2$ in humans. The method of administration was left carotid aortic infusion method. These data are expressed according to lineages of bone marrow cell in Table 3a and 3b.

TABLE 3a

| | | wbc | wbc | wbc | Platelet | Plt | plt |
|---|---|---|---|---|---|---|---|
| chemo | mean | 9.2 | 0.7 | 3.2 | 759.0 | 63.3 | 164.0 |
| | sd | 3.6 | 0.2 | 1.6 | 260.5 | 59.0 | 91.0 |
| | n | 7 | 4 | 3 | 7 | 4 | 3 |
| | | wbc | wbc | Wbc | Platelet | Plt | plt |
| chemo + | mean | 7.1 | 1.4 | 5.2 | 772.3 | 132.0 | 1559.0 |
| | sd | 2.7 | 1.1 | 1.7 | 171.5 | 36.8 | 567.1 |
| | n | 4 | 2 | 2 | 4 | 2 | 2 |
| | | wbc | wbc | wbc | Platelet | Plt | plt |
| chemo + | mean | 9.5 | 2.8 | 8.6 | 936.5 | 554.0 | 1950.0 |
| NAC + | sd | 6.0 | 0.4 | 3.6 | 186.0 | 147.1 | 134.4 |
| | n | 2 | 2 | 2 | 2 | 2 | 2 |

TABLE 3b

| | wbc base | wbc d6 | wbc d9 | plt base | plt d6 | plt d9 |
|---|---|---|---|---|---|---|
| chemo + BSO | | | | | | |
| mean | 6.8 | 0.8 | 5.4 | 930 | 92 | 387 |
| +/−sd | +/−?0.8 | +/−0.2 | +/−1.1 | +/−63 | +/−28 | +/−139 |
| number | 11 | 11 | 6 | 11 | 11 | 6 |
| BSO + chem + NAC | | | | | | |
| mean | 8.4 | 2.2 | 7.6 | 818 | 341 | 1560 |
| +/−sd | +/−1.5 | +/−0.3 | +/−1.2 | +/−99 | +/−79 | +/−194 |
| number | 9 | 9 | 6 | 9 | 9 | 6 |

These data show the synergistic effect of a combination of STS and NAC as the combined thiol-based chemoprotectant agents administered according to the inventive process.

EXAMPLE 5

This example provides the results of an in vitro experiment using a combination of a taxane (paclitaxel) with a paclitaxel-cytotoxic enhancing agent BSO and a glutathione-reviving agent NAC in cultured tumor cells. Paclitaxel is cytostatic in cultured cells at concentrations from 1 to 10 micromolar, that is, the tumor cells do not grow but they are not killed either. At 20 uM, paclitaxel begins to be cytotoxic and at 30 uM it is completely toxic in cultured tumor cells. When the tumor cells were pretreated cells with BSO, paclitaxel addition was completely cytotoxic in vitro at doses as low as 5 uM.

NAC did not change the dose response for paclitaxel alone. However, NAC completely reversed the enhanced toxicity from the BSO treatment, returning paclitaxel concentration effects to the non-BSO level. This experiment was repeated twice with the data provided in Table 4.

TABLE 4

| Treatment | paclitaxel dose | live cells (WST fluorescence) |
| --- | --- | --- |
| paclitaxel alone | 5 | 1.274 +/− .071 |
|  | 20 | 0.771 +/− .056 |
| paclitaxel + NAC | 5 | 1.369 +/− .061 |
|  | 20 | 0.823 +/− .094 |
| BSO + paclitaxel | 5 | 0.056 +/− .004** |
|  | 20 | 0.045 +/− .004** |
| BSO + paclitaxel + NAC | 5 | 1.419 +/− .095* |
|  | 20 | 0.732 +/− .100* |

*significantly different from BSO and paclitaxel
**significantly different from paclitaxel alone

EXAMPLE 6

Chemoprotection Against Cytotoxicity

Figure 3A:
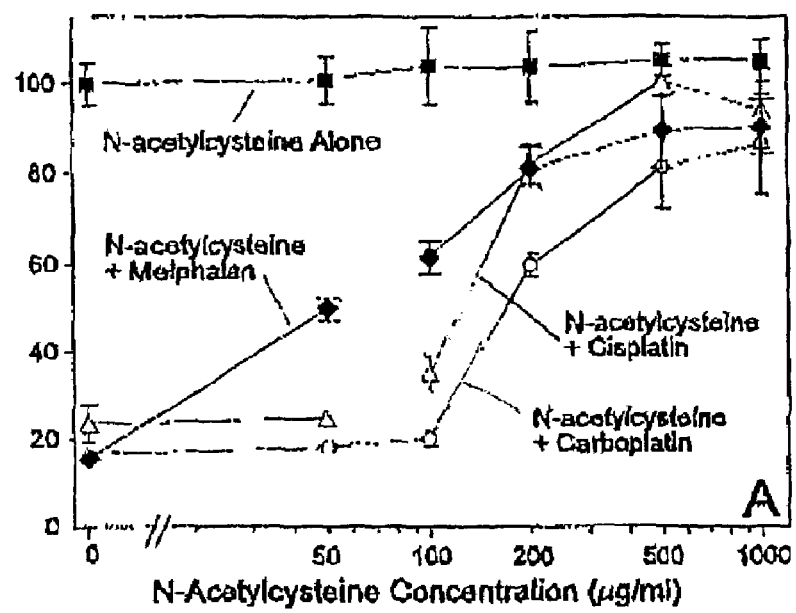
FIG. 3A shows dose/response for N-acetylcysteine chemoprotection.
Figure 3B:
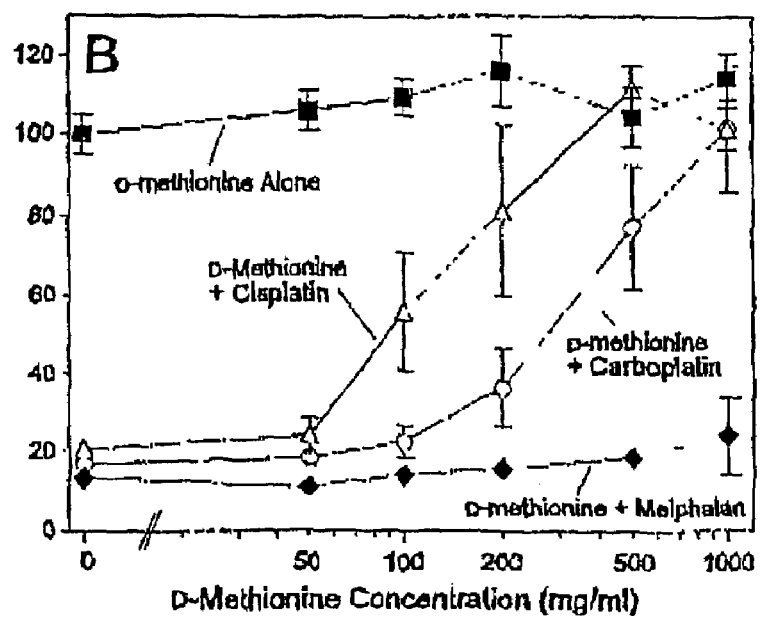
FIG. 3B shows dose/response for D-methionine chemoprotection. Cytotoxicity was assessed in cultured LX-1 SCLC cells, 1×10$^4$ cells per well in 96 well plates, using the WST colorometric assay. Cells were treated with approximately 90% lethal dose of chemotherapy (melphalan=20 µg/ml, carboplatin=200 µg/ml, cisplatin=20 µg/ml). Chemoprotectant was added at the indicated concentration of N-acetylcysteine shown in FIG. 3A or D-methionine shown in FIG. 3B either alone (n) or immediately following chemotherapy. Data are expressed as the percentage of live cells compared to untreated control samples (without chemotherapy) and each point represents the mean±standard deviation of 4 wells.

The dose/response for rescue from chemotherapy cytotoxicity was evaluated for four different small molecular weight sulfur containing chemoprotectants. Each chemotherapeutic agent was used at a concentration affording approximately 90% lethality in the absence of BSO (20 μg/ml melphalan, 200 μg/ml carboplatin, 15 μg/ml cisplatin). Over all, N-acetylcysteine was the most effective of the thiol agents tested, on a μg/ml basis. The concentration dependence for protection with N-acetylcysteine in comparison to D-methionine is shown in FIGS. 3A and 3B, and Table 5 shows the EC50 for protection afforded by each protective agent. As shown in FIG. 3A AND Table 5, the cytotoxicity of each alkylator was reduced by 75–90% by concurrent administration of N-acetylcysteine, but N-acetylcysteine was more active against melphalan (EC50=74±18 μg/ml) than the platinum agents. In contrast, as shown in FIG. 3B and Table 5, D-methionine did not protect against melphalan toxicity at the doses tested (50 to 1000 μg/ml), although it was highly protective against cisplatin toxicity, with a half-maximal concentration of 140±41 μg/ml. The maximum magnitude of protection was variable between experiments, ranging from about 70% to 100% protection, and protection was consistently less for carboplatin than for cisplatin or melphalan. All agents tested required a significantly higher dose to protect against carboplatin than against cisplatin or melphalan. On a μg/ml basis, glutathione ethyl ester was the least effective protective agent.

Chemotherapy agents were fixed at the 90% lethal dose for each agent. Each EC50 measurement comprised 6 concentrations with 4 wells per concentration, and each dose response was performed twice for each protectant. EC50 concentrations, in μg/ml are reported as the average±pooled standard deviation for two independent experiments. For the combination of D-methionine with melphalan, protection was not detected. For each chemoprotectant, t test comparisons were done for melphalan versus cisplatin, cisplatin versus carboplatin, and carboplatin versus melphalan, and significant differences are indicated (=P<0.01; *=P<0.001).

TABLE 5

| Protection against chemotherapy cytotoxity | | | | |
| --- | --- | --- | --- | --- |
| | Chemoprotective agent EC50 (μg/ml) | | | |
| chemotherapy | N-acetylcysteine | Sodium thiosulfate | D-methionine | Glutathione ethyl ester |
| Melphalan | 74 ± 18*** | 110 ± 78 | None*** | 303 ± 124*** |
| Cisplatin | 151 ± 15** | 86 ± 76** | 140 ± 41*** | 530 ± 30*** |
| Carboplatin | 200 ± 15*** | 442 ± 203** | 379 ± 123*** | 995 ± 48*** |

EXAMPLE 7

Cytoenhancement and Chemoprotection in Combination

Figure 4A:
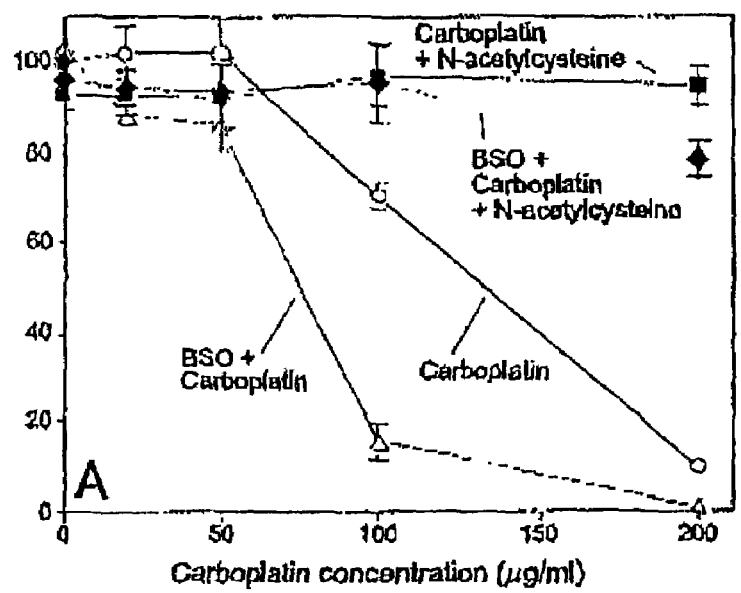
FIGS. 4A and 4B show cytoenhancement and chemoprotection.

The effects of BSO cytoenhancement and thiol chemoprotection on the dose/response relationships for cytotoxicity of the alkylating chemotherapeutics were evaluated in the B.5 LX-1 cells. BSO cytoenhancement consisted of preincubation with 100 μM BSO for about 18–24 hours prior to addition of chemotherapy, and rescue consisted of 1000–2000 μg/ml of thiol chemoprotectant added immediately after chemotherapy. As shown in FIG. 4A and Table 6, BSO consistently decreased the EC50 for cytotoxicity and increased the maximum degree of toxicity. The specific case of carboplatin and N-acetylcysteine is shown in FIG. 4A. Glutathione depletion with BSO increased carboplatin cytotoxicity, reducing the EC50 by 48% (P<0.01). As detailed in Table 6, similar BSO cytoenhancement was found with melphalan (53% reduction of EC50, P<0.001), while the EC50 for cisplatin was reduced only 29% (P<0.05). Chemoprotection with N-acetylcysteine blocked carboplatin toxicity as well as BSO-enhanced cytotoxicity. Similar chemoprotection was found with additional thiol agents, sodium thiosulfate and glutathione-ethyl ester, but D-methionine was only effective against the platinum agents.

Figure 4B:
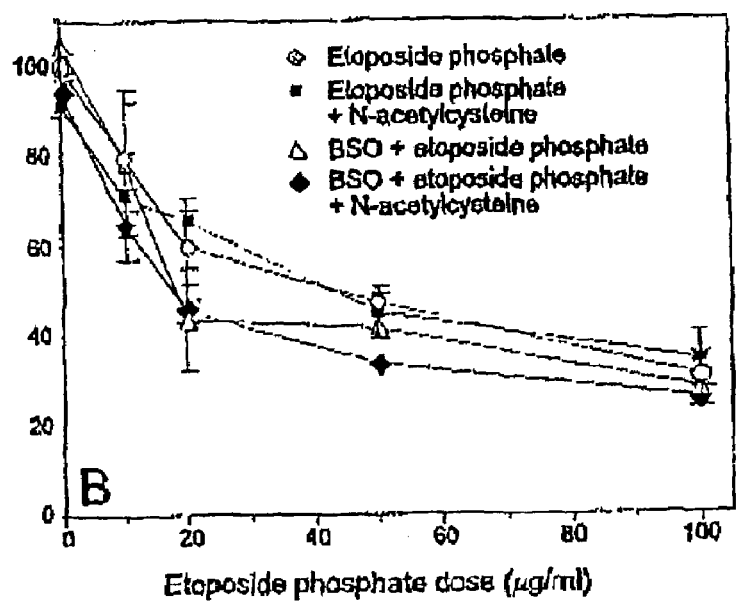

Cytoenhancement and chemoprotection against non-alkylating chemotherapeutic agents was also evaluated. As shown in FIG. 4B, Glutathione depletion with BSO did not increase the cytotoxicity of etoposide phosphate, nor did N-acetylcysteine decrease the cytotoxicity of etoposide phosphate. Similarly, no enhancement or protection was found with methotrexate or doxorubicin in the B.5 LX-1 cells, although carcinoma cells of gastric origin showed some enhancement with BSO (data not shown). Interestingly, although the growth inhibitory dose of taxol (approximately 10 nM) was not altered by BSO, glutathione depletion did shift the cytotoxic dose of taxol from 15 μM to 2 μM, and this enhanced cytotoxicity was completely reversed with N-acetylcysteine (not shown).

Figure 5:
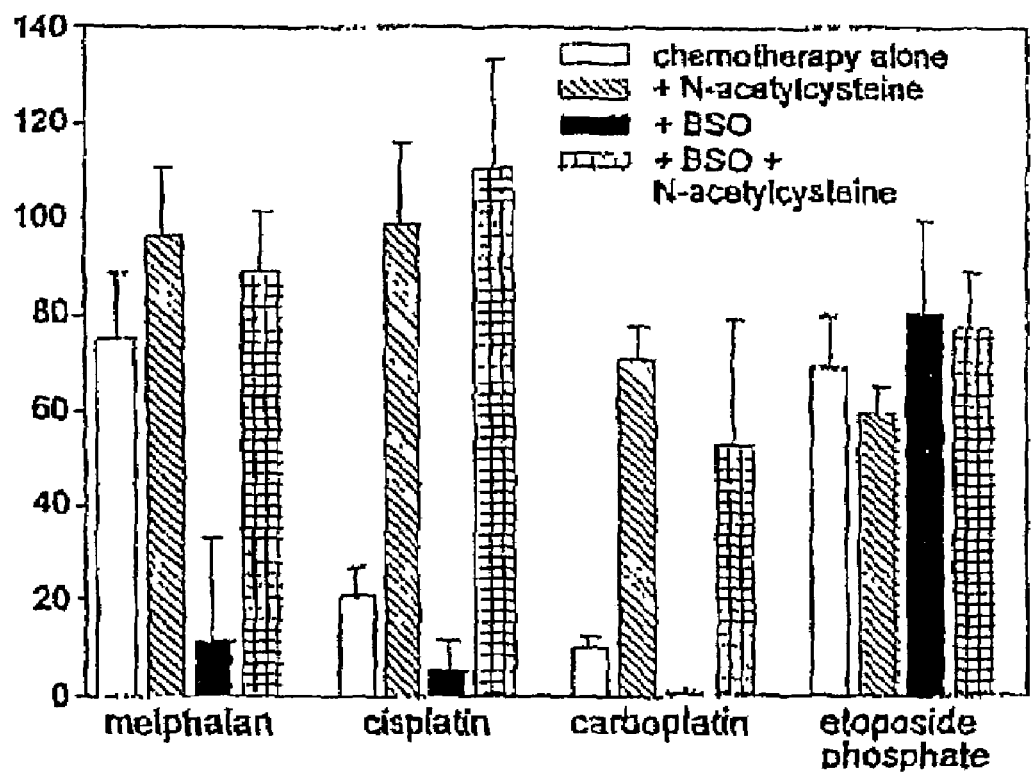
FIG. 5 shows cytoenhancement and chemoprotection in fibroblasts. Cytotoxicity was assessed in GM294 human fibroblasts, $1\times10^4$ cells per well in 96 well plates, using the WST colorometric assay. Cells were pretreated with or without BSO, 100 μM for 18 hours prior to addition of chemotherapeutics (melphalan=10 μg/ml, carboplatin=100 μg/ml, cisplatin=7.5 μg/ml, etoposide phosphate 100 μg/ml) either alone (open bar), or with N-acetylcysteine rescue, (1000 μg/ml N-acetylcysteine, striped bar), BSO cytoenhancement (black bar), or BSO cytoenhancement and N-acetylcysteine rescue (cross hatched bar). Data are expressed as the percentage of live cells compared to control samples (without chemotherapy) and each point represents the mean±s.d. of 4 wells.

Whether the cytoenhancement and chemoprotection seen in the B.5 LX-1 SCLC cells was a generalized phenomenon was evaluated by testing similar experimental conditions in the GM294 human fibroblast cell strain. Cells were treated with or without chemotherapy at the approximately half maximal dose found in the B.5 LX-1 cells, with or without pretreatment with BSO. As shown in FIGS. 3A and 3B, although melphalan, cisplatin and carboplatin were all somewhat more cytotoxic in the fibroblasts as compared to the tumor cells, nevertheless BSO enhanced the toxicity of all three alkylators. In fibroblasts, N-acetylcysteine was partially to completely chemoprotective against the cytotoxicity induced by melphalan, cisplatin and carboplatin, independent of BSO treatment. As shown in FIG. 5, neither BSO cytoenhancement nor N-acetylcysteine chemoprotection affected the cytotoxicity of etoposide phosphate in fibroblasts.

Half-maximal cytotoxic concentrations (EC50) are expressed as µg/ml. Each EC50 measurement comprised 6 concentrations with 4 wells per concentration, and each dose response was performed in triplicate for each chemotherapeutic agent. Data are reported as the mean±pooled standard deviation for three independent experiments. P values are shown for the reduction in EC50 by BSO treatment (*=P<0.05, =P<0.01, *=P<0.001).

TABLE 6

Effect of BSO on the cytotoxicity of alkylating chemotherapeutics

| | Chemotherapy EC50 (µg/ml) | | |
|---|---|---|---|
| | Melphalan | Cisplatin | Carboplatin |
| Without BSO | 13.8 ± 1.8 | 8.9 ± 2.4 | 103 ± 21 |
| + BSO | 6.4 ± 0.6*** | 6.4 ± 0.9* | 55 ± 15** |

EXAMPLE 8

Time Dependence for Chemoprotectant Rescue from Chemotherapy Cytotoxicity

Figure 6:
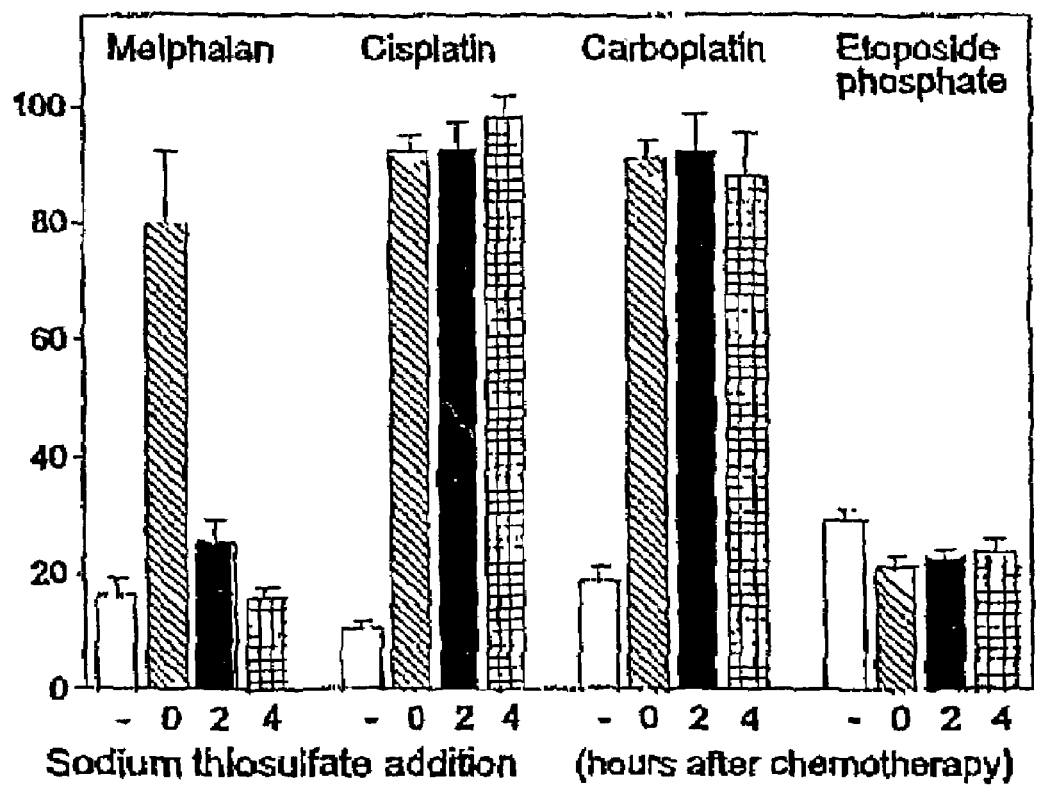
FIG. 6 shows time dependence for rescue of chemotherapy cytotoxicity. Chemotherapy cytotoxicity was assessed in cultured LX-1 SCLC cells ($1\times10^4$ cells/well in 96 well plates) using the WST colorometric assay. Cells were treated with melphalan at 20 μg/ml, carboplatin 200 μg/ml, cisplatin 10 μg/ml, or etoposide phosphate 200 μg/ml. Cells then received either no protectant (open bars), or sodium thiosulfate, 2000 μg/ml, added immediately (striped bars), 2 hours (black bars) or 4 hours (cross hatched bars) after chemotherapy. Data are expressed as the percentage of live cells compared to control samples (without chemotherapy) and each point represents the mean±standard deviation of 4 wells.

How long the addition of chemoprotectant could be delayed after treatment with chemotherapy and remain effective was evaluated. Cells were treated with doses of chemotherapy providing approximately 90% lethality, for melphalan (20 µg/ml), carboplatin (200 µg/ml), or cisplatin (15 µg/ml). The thiol chemoprotectants were added either concurrently with chemotherapy or up to 8 hours after chemotherapy. For melphalan, chemoprotection was reduced if administration of STS was delayed for 2 hours, whereas sodium thiosulfate was still protective for the platinum chemotherapeutics if delayed up to 4 hours after treatment as shown in FIG. 6. Similarly, delayed administration of N-acetylcysteine and glutathione ethyl ester reduced their protective activity against melphalan cytotoxicity, whereas both agents maintained protective activity against platinum cytotoxicity. Separately, all three agents were completely protective if added within 1 hour of melphalan, rather than 2 hours as shown in FIG. 6. Chemoprotection was not effective against etoposide phosphate cytotoxicity at any time point.

The time dependence of D-methionine rescue of cisplatin cytotoxicity was also evaluated. Unlike chemoprotection with thiosulfate, N-acetylcysteine, or glutathione ethyl ester, the protection afforded by D-methionine was significantly reduced by delayed administration. If delayed for 2 hours after cisplatin, D-methionine protection was reduced by 41.2±10.2% compared to the maximal protection seen with simultaneous addition, while delaying D-methionine to 4 hours reduced protection by 66.1±4.5% compared with simultaneous addition. Pretreatment with D-methionine for 30 min prior to addition of cisplatin did not increase the amount of protection compared to simultaneous addition.

EXAMPLE 9

Effects of Cytoenhancement and Chemoprotection on Apoptosis

Figure 7A:
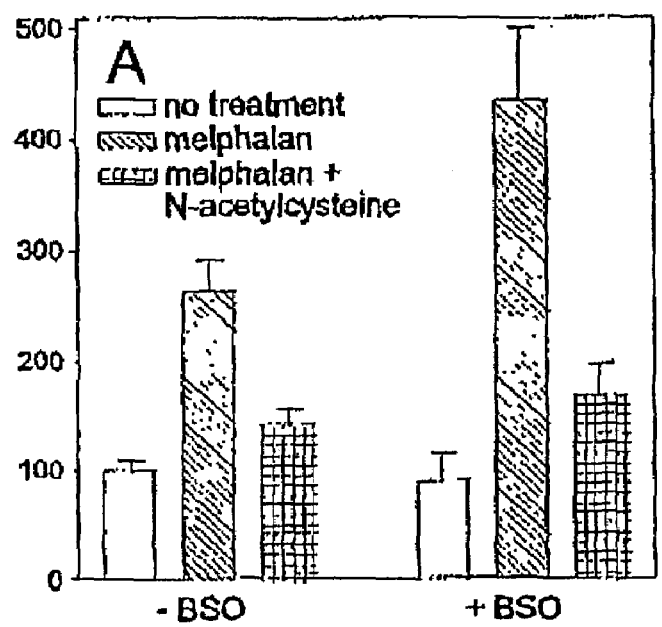
FIGS. 7A and 7B show the effect of cytoenhancement and chemoprotection on apoptosis.
Figure 7B:
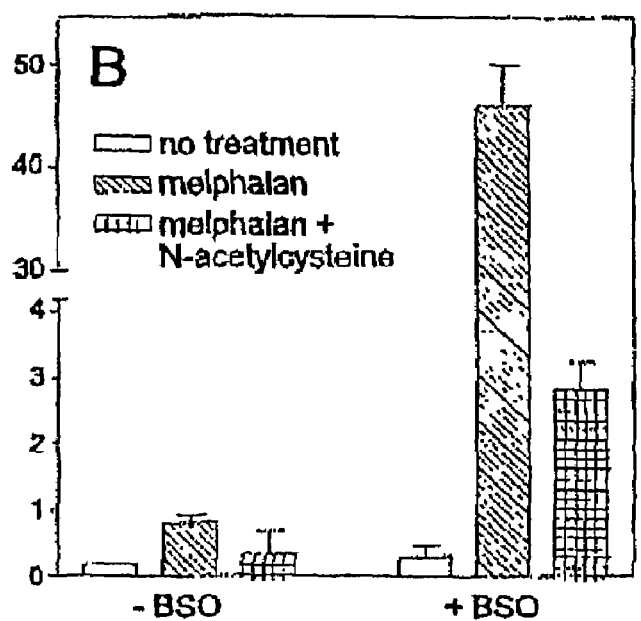

Apoptosis was evaluated by measuring Caspase-2 enzymatic activity and by in situ TUNEL staining. Treatment of B.5 LX-1 cells with melphalan resulted in an increase in Caspase-2 activity that was amplified by BSO pretreatment at low melphalan concentrations as shown in FIG. 7A. The increase in caspase activity was variable between experiments and ranged from 50–100% at 7–8 h to 250–600% at 20–24 h after treatment with melphalan. TUNEL staining also demonstrated melphalan-induced apoptosis. In the experiment shown in FIG. 7B, TUNEL staining after melphalan treatment was positive in 29 of 3643 cells, compared to 7 of 4395 cells in the untreated control, and BSO treatment prior to melphalan increased the positive staining to 800 of 1699 cells. In both the caspase-2 assay as shown in FIG. 7A and the TUNEL staining assay as shown in FIG. 7B, the effect of melphalan on apoptosis was reduced by the chemoprotectant N-acetylcysteine. In both assays, activity was maximal with low doses of melphalan, or with a 1 hour pulse treatment with the doses used in the cytotoxicity assays. Continuous treatment with the cytotoxic dose of melphalan actually reduced caspase-2 activity and TUNEL staining.

Cisplatin and carboplatin were less effective than melphalan at inducing caspase activity. Over a range of doses (100, 150, or 200 µg/ml carboplatin, and 5, 10, or 15 µg/ml cisplatin) and times (8, 12, 16, 20, 24 h), each platinum agent increased Caspase-2 activity by 50–100%. No significant amplification of caspase activity was induced by BSO treatment. Additionally, no reduction in caspase enzymatic activity could be detected after addition of N-acetylcysteine, and in some experiments treatment with N-acetylcysteine actually increased cisplatin- or carboplatin-induced caspase activity. Samples of the cells used in the caspase and TUNEL assays were also evaluated for membrane permeability by trypan blue exclusion. In experiments producing negative results with the caspase-2 or TUNEL assays, trypan blue exclusion showed high numbers of non-viable cells after treatment with carboplatin or cisplatin and this was increased by BSO treatment.

EXAMPLE 10

Biodistribution of Radiolabeled NAC

Figure 8:
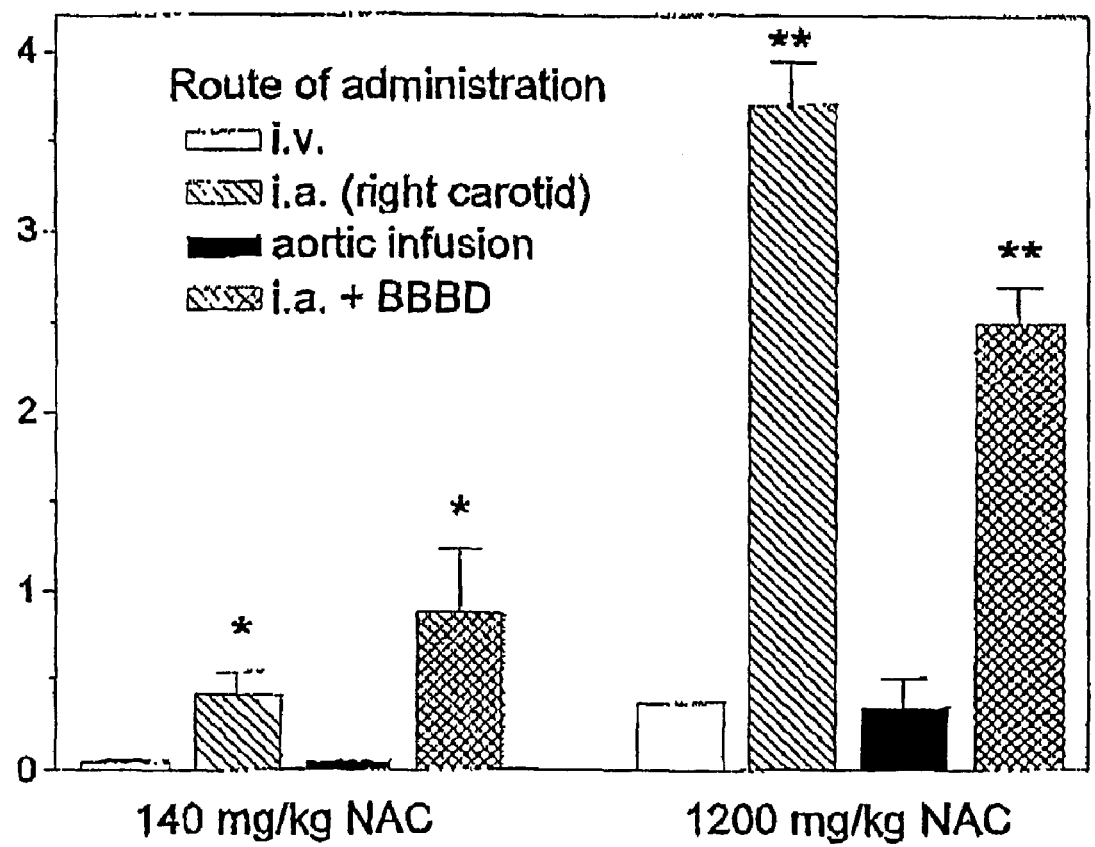
FIG. 8 shows the results of NAC delivery to rat brain. Radiolabeled NAC in combination with unlabeled low dose NAC (140 mg/kg) or high dose NAC (1200 mg/kg) was administered to rats with the following routes of infusion: i.v. (open bars), intra-arterially into the right carotid artery (striped bars), intra-arterial via the left carotid artery with left internal artery occlusion (aortic infusion) (black bars), and intra-arterial (right carotid) with BBBD (cross hatched bars). Radiolabel in tissue homogenates is expressed as the mean and standard error of the % administered dose of 14C-NAC per gram of tissue (n=3 rats per group). Significant differences from i.v. delivery are indicated by *P<0.05 and **P<0.001.

The method of administration of NAC and its biodistribution was tested. Intra-arterial infusion retrograde via the left external carotid artery, with transient left internal artery occlusion, was evaluated as a mechanism to essentially perfuse via the descending aorta with limited delivery to the brain. When NAC was administered i.v., negligible amounts were found in brain as determined by the percent administered dose of 14C-NAC per gram of tissue as shown in FIG. 8. Intra-arterial delivery in the right internal carotid artery resulted in high levels of radiolabel in the right cerebral hemisphere, and this was not increased by BBBD. However, aortic infusion minimized brain delivery of NAC as shown in FIG. 8. At the low dose of NAC (140 mg/kg), aortic infusion decreased liver delivery and increased kidney delivery, where as there was no change in liver and kidney delivery at high dose (1200 mg/kg) NAC (data not shown). The serum concentration of NAC 10 min after administration of 1200 mg/kg was 2.4 0.6 mg/ml (n=6) as determined by radiolabel remaining in the blood.

EXAMPLE 11

Toxicity of NAC

A dose escalation of NAC was performed in the rat. Initial doses of 140–800 mg/kg NAC administered i.v. immediately after chemotherapy (n=4), were well tolerated but provided no detectable bone marrow protection. Doses of NAC above 1200 mg/kg (n=3) were toxic whereas there was no toxicity at 1200 mg/kg. Therefore, 1200 mg/kg of NAC was used for the bone marrow protection studies, except when administered in conjunction with STS where a dose of 1000 mg/kg was used due to volume considerations.

Figure 9:
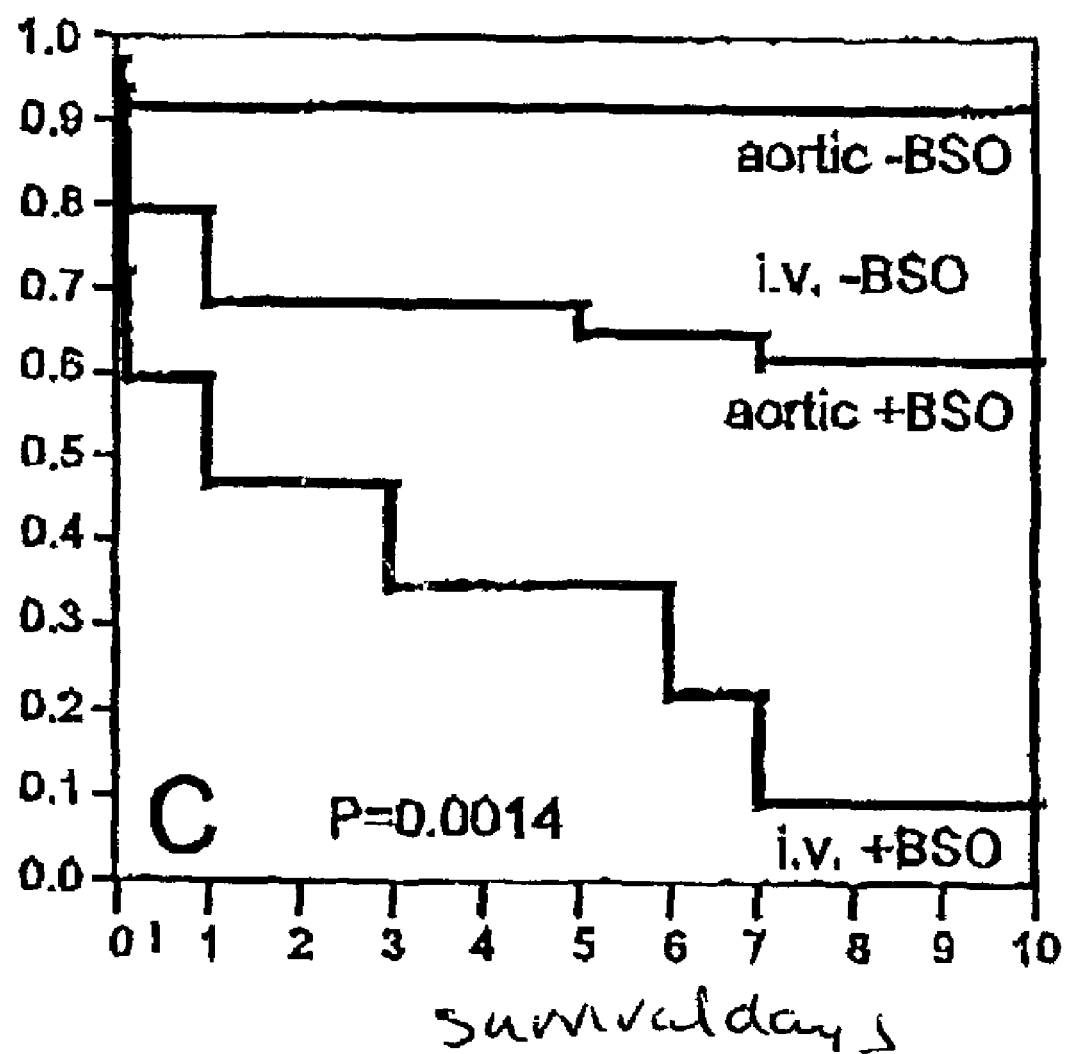
FIG. 9 represents tests showing the effect of NAC route of administration on mortality+/−BSO. A Kaplan-Meier product limit analysis was used to evaluate the mortality due to chemoprotection with NAC. Rats were treated with or without BSO (10 mg/kg i.p. b.i.d.×3, black bars) prior to treatment with chemotherapy (Carboplatin 200 mg/m2, etoposide phosphate 100 mg/m2, melphalan 10 mg/m2). Chemoprotection consisted of NAC (1200 mg/m2) or NAC (1000 mg/m2) plus STS (8 g/m2) given either i.v. (n=17 BBSO, n=8+BSO) or by aortic infusion (n=19 BBSO, n=28+BSO). P=0.0014 by Wilcoxon analysis.

The toxicity of NAC was determined when infused for bone marrow protection. As shown in FIG. 9. the mortality due to NAC was significantly dependent on the route of administration, with i.v. administration significantly more toxic than aortic infusion (P=0.0014). Pretreatment with BSO markedly enhanced the toxicity of NAC. Groups given i.v. NAC after BSO treatment were halted early due to excessive mortality, with a stopping rule of 75% mortality within n=4 animals. In selected animals (n=21) from all groups, blood pressure monitoring indicated most animals that expired experienced persistent acute hypotension, suggesting cardiac toxicity. Of particular note, however, there was no mortality nor any evidence of toxicity in 12 animals, without BSO, giving 1200 mg/kg NAC by aortic infusion 30 minutes prior to chemotherapy.

EXAMPLE 12

Effect of NAC on Chemotherapy-induced Bone Marrow Toxicity

Chemoprotection against chemotherapy-induced bone marrow toxicity was determined in BSO treated and untreated animals given i.a. carboplatin, etoposide phosphate, and melphalan. NAC with or without STS was administered either about 30 minutes prior to chemotherapy or immediately after chemotherapy, and was administered either i.v. or by aortic infusion. Chemoprotection was found with NAC as shown by increased blood counts (white blood cells, granulocytes, platelets) at the nadir, compared to no chemoprotectant as shown in Table 7 and Table 8. Chemoprotection was effective whether or not animals were pretreated with BSO as shown in FIG. 10, and the magnitude of the chemotherapy-induced bone marrow toxicity nadir was minimized and recovery to normal platelet levels was improved.

TABLE 7

Protection against chemotherapy-induced myelosuppression

| Treatment | Rats | White Cell Nadir | Granulocyte Nadir | Platelet Nadir |
|---|---|---|---|---|
| No protectant | N = 6 | 24.5 ± 5.8 | 20.7 ± 11.0 | 22.7 ± 8.7 |
| NAC i.v. post chemo | N = 6 | 46.0 ± 6.5* | 57.9 ± 8.8* | 36.8 ± 10.4 |

TABLE 7-continued

Protection against chemotherapy-induced myelosuppression

| Treatment | Rats | White Cell Nadir | Granulocyte Nadir | Platelet Nadir |
|---|---|---|---|---|
| NAC i.v. 30 min prior | N = 8 | 51.4 ± 9.4 | 93.5 ± 28.1 | 53.3 ± 12.7 |
| NAC aortic infusion post chemo | N = 6 | 25.9 ± 4.9 | 36.6 ± 17.0 | 26.8 ± 9.3 |
| NAC aortic infusion 30 min prior | N = 6 | 69.7 ± 19.3 | 206.2 ± 125.1* | 59.3 ± 17.9 |
| NAC aortic infusion 30 min prior + STS post chemo | N = 6 | 53.8 ± 12.8* | 83.4 ± 21.3* | 47.0 ± 11.5 |

The mean and standard error are shown for nadir blood counts as a percent of baseline.
*indicates $P < 0.05$ compared to no protectant, by Wilcoxon/Kruskal-Wallis rank sums tests.

TABLE 8

Protection against BSO-enhanced chemotherapy-induced myelosuppression

| Treatment | Rats | White Cell Nadir | Granulocyte Nadir | Platelet Nadir |
|---|---|---|---|---|
| No protectant | N = 11 | 12.9 ± 3.5 | 3.5 ± 1.3 | 9.1 ± 2.3 |
| NAC aortic infusion post chemo | N = 7 | 13.9 ± 4.2 | 19.8 ± 14.7 | 11.7 ± 3.5 |
| NAC aortic infusion 30 min prior | N = 9 | 20.1 ± 2.7 | 115.4 ± 68.8* | 23.1 ± 6.2 |
| NAC aortic infusion 30 min prior + STS post chemo | N = 7 | 30.5 ± 6.5* | 121.0 ± 40.2* | 39.0 ± 74* |

The mean and standard error are shown for nadir blood counts as a percent of baseline.
*indicates $P < 0.05$ compared to no protectant, by Wilcoxon/Kruskal-Wallis rank sums tests.

Figure 10A:
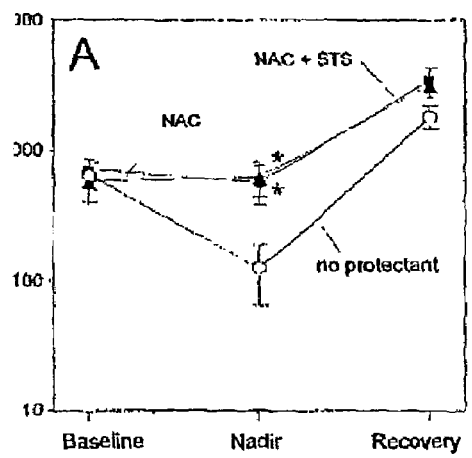
FIGS. 10A–10D show the results of tests on chemoprotection for chemotherapy-induced myelosuppression. Rats received tri-drug chemotherapy (Carboplatin 200 mg/m2, etoposide phosphate 100 mg/m2, melphalan 10 mg/m2), with (triangles, squares) or without (circles) chemoprotection. Blood counts were determined prior to chemotherapy, at the blood nadir (6 days), and in the recovery phase (9 days after treatment). Chemoprotection was with NAC (1200 mg/kg) administered via aortic infusion 30 min prior to chemotherapy (triangles) or NAC prior to chemotherapy and STS (8 g/m2) immediately after chemotherapy (squares).
Figure 10C:
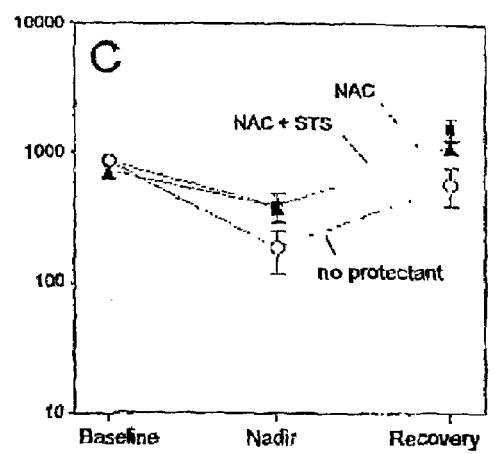

In animals that did not undergo BSO treatment, pretreatment with NAC (1200 mg/kg) by aortic infusion, with or without follow-up with STS, was the best treatment strategy as shown in FIGS. 10A and 10C. As shown in FIG. 10A, the chemotherapy-induced decrease in granulocyte counts was completely blocked (p<0.05) and platelet toxicity was reduced as shown in FIG. 10C by aortic infusion of NAC 30 minutes prior to chemotherapy.

Figure 10B:
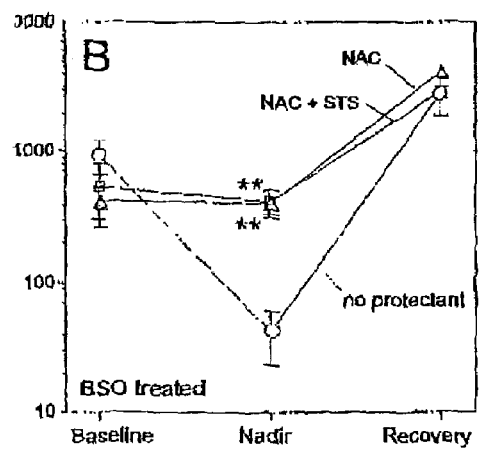
Figure 10D:
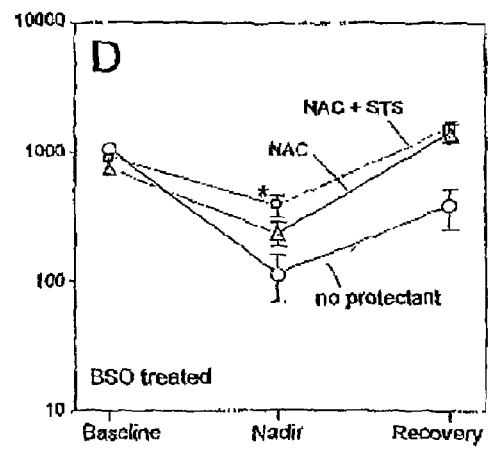

In animals pretreated with BSO, good protection for granulocytes was provided by aortic infusion of NAC about 30 min prior to chemotherapy, but the best protection and the least mortality was provided by NAC aortic infusion before and STS immediately after chemotherapy as shown in FIGS. 10B and 10D. As shown in FIG. 10B, the combination chemoprotection (NAC and STS) regimen significantly blocked the toxicity for granulocytes (p<0.01) and, as shown in FIG. 10D, platelets (p<0.01) compared to animals that received no chemoprotection. Chemoprotection also significantly enhanced the platelet recovery from chemotherapy. STS alone did not give consistent bone marrow protection (data not shown).

As noted, the discussion above is descriptive, illustrative and exemplary and is not to be taken as limiting the scope defined by any appended claims.

We claim:

1. A method for treating or mitigating myelosuppression, comprising:
   administering intravenously a high-dose thiol based chemoprotectant agent wherein the high-thiol based chemoprotectant agent is N-acetylcysteine(NAC).

2. The method for treating or mitigating myelosuppression of claim 1 wherein the high-dose thiol based chemoprotectant agent is from about 400 mg/m$^2$ to about 1200 mg/m$^2$ per procedure.

* * * * *